United States Patent [19]

Spicer et al.

[11] B 3,989,835

[45] Nov. 2, 1976

[54] METHOD OF USING 6-SUBSTITUTED AMINO PHENYL-2,3,5,6-TETRA-HYDRO[2,1-b]THIAZOLES FOR CONTROLLING GASTROINTESTINAL NEMATODES

[75] Inventors: Larry Dean Spicer, Princeton; John James Hand, Trenton, both of N.J.

[73] Assignee: American Cyanamid Company, Stamford, Conn.

[22] Filed: Nov. 7, 1974

[21] Appl. No.: 521,711

[44] Published under the second Trial Voluntary Protest Program on February 10, 1976 as document No. B 521,711.

Related U.S. Application Data

[60] Division of Ser. No. 416,464, Nov. 16, 1973, Pat. No. 3,899,583, which is a division of Ser. No. 289,016, Sept. 14, 1972, abandoned, which is a continuation-in-part of Ser. No. 174,939, Aug. 25, 1971, abandoned, which is a continuation-in-part of Ser. No. 22,701, March 25, 1970, Pat. No. 3,673,205.

[52] U.S. Cl. .............................................. 424/270
[51] Int. Cl.$^2$ ..................................... A61K 31/425
[58] Field of Search .................................. 424/270

[56] References Cited
UNITED STATES PATENTS 3,505,346    4/1970    Berkelhammer et al. .......... 424/270

Primary Examiner—Sam Rosen
Attorney, Agent, or Firm—Denis A. Polyn

[57] ABSTRACT

The preparation of compounds of the type 6-(mono substituted phenyl)-5,6-dihydro or 2,3,5,6-tetrahydroimidazo[2,1-b]thiazoles and the pharmaceutically acceptable salts thereof, is described. The use of said compounds for treating helminthiasis in warm-blooded animals is also described.

4 Claims, No Drawings

METHOD OF USING 6-SUBSTITUTED AMINO PHENYL-2,3,5,6-TETRA-HYDRO[2,1-b]THIAZOLES FOR CONTROLLING GASTROINTESTINAL NEMATODES

This application is a division of application Ser. No. 416,464, filed Nov. 16, 1973, now U.S. Pat. No. 3,899,583, which is a division of application Ser. No. 289,016, filed Sept. 14, 1972, now abandoned, which is a continuation-in-part of our application Ser. No. 174,939, filed Aug. 25, 1971, now abandoned, which is a continuation-in-part of application Ser. No. 22,701, filed Mar. 25, 1970, now U.S. Pat. No. 3,673,205.

BACKGROUND OF THE INVENTION

A number of 6-substituted-imidazo[2,1-b]thiazoles are generically disclosed by Raeymakers et al. in their U.S. Pat. Nos. 3,274,209, issued Sept. 20, 1966, and 3,364,112, issued Jan. 16, 1968. Use of these compounds as anthelmintic agents is also suggested and data for several compounds are described. The compounds actually exemplified, however, have their limitations. This is especially evident when such compounds are employed for control of whipworms, particularly in Canidae. While both the optically inactive dl-6-phenyl-2,3,5,6-tetrahydroimidazo[2,1-b]thiazole of Raeymakers et al. and the optically active l-6-phenyl-2,3,5,6,-tetrahydroimidazo[2,1-b]thiazole of Bullock, U.S. Pat. 3,463,786, issued Aug. 26, 1969, are highly effective against most helminths, they are not sufficiently active against whipworms, especially in dogs, to permit the use of a dosage level which will effectively control whipworm infestations while maintaining a margin of safety considered to be desirable or acceptable.

DESCRIPTION OF THE INVENTION

Surprisingly, we have now found that effective and safe whipworm control in warm-blooded animals can be obtained with compounds of the formula below and their pharmaceutically acceptable salts.

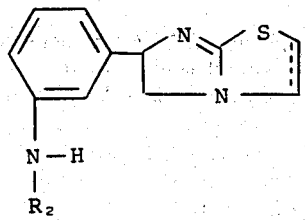

wherein $R_2$ is selected from the group consisting of pyridylmethyl, naphthoyl, furoyl, and adamantyl carbonyl, and ==== is a single or double bond and the pharmaceutically acceptable salts thereof.

Broadly speaking, the compounds of this invention can be prepared by a process for the preparation of a compound or the pharmaceutically acceptable acid salt thereof having the formula:

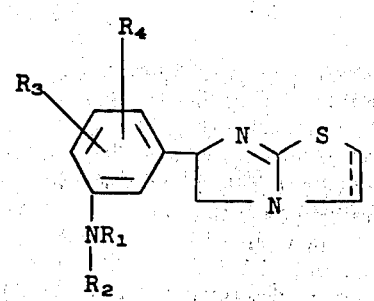

wherein $R_1$ and $R_2$ are selected from the group consisting of hydrogen, alkyl $C_1$–$C_{10}$, alkenyl $C_2$–$C_8$, cycloalkyl $C_3$–$C_7$, hydroxyloweralkyl, loweralkanoyloxyloweralkyl, loweralkoxyloweralkyl, benzyl, substituted benzyl, phenylethyl, substituted phenylethyl, mono- and dinitrophenyl, 2- and 4-pyridyl, 2- and 4-pyrimidinyl, 2-thiazolyl, pyridylmethyl, furfuryl, tetrahydrofurfuryl, $R_5$—C(O) wherein $R_5$ is selected from the group consisting of hydrogen, alkyl $C_1$–$C_9$, alkenyl $C_2$–$C_7$, cycloalkyl $C_3$–$C_7$, haloalkyl $C_1$–$C_6$, aminoalkyl $C_1$–$C_6$, monoloweralkylaminoloweralkyl, diloweralkylaminoloweralkyl, piperidinoloweralkyl, pyrrolidinoloweralkyl, morpholinoloweralkyl, loweralkoxyloweralkyl, phenyl, substituted phenyl, furyl, tetrahydrofuryl, naphthyl, alkoxy $C_1$–$C_8$, amino, monoloweralkylamino, diloweralkylamino, piperidino, pyrrolidino, adamantane and morpholino, and where

taken together may represent piperidino, pyrrolidino, or morpholino ring or the group (loweralkyl)$_2$-NCH=N—; and $R_3$ and $R_4$ are selected from the group consisting of hydrogen, halogen, and nitro, the term substituted covers monohalo, dihalo, trihalo, mononitro, dinitro, monoloweralkyl, diloweralkyl, triloweralkyl, monoloweralkoxy, diloweralkoxy, and triloweralkoxy; and the term halogen covers fluoro, chloro, bromo, and iodo; with the proviso that when $R_3$ and $R_4$ are both hydrogen not more than one member from the group $R_1$ and $R_2$ can be hydrogen, and ==== represents single or double bond, comprising reacting a compound of the formula:

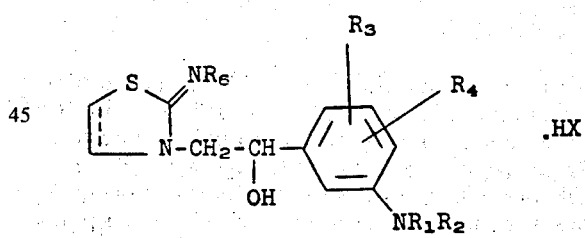

where $R_1$, $R_2$, $R_3$, $R_4$ are as described above and $R_6$ is hydrogen or loweralkanoyl, preferably acetyl and X is an anion, with (a) concentration sulfuric acid and treating the thus formed product with a base, preferably an alkali metal hydroxide or ammonium hydroxide, or (b) thionyl chloride at a temperature of from 40°C. to 75°C. and treating the reaction product with acetic anhydride at 50°C. to 140°C., removing excess loweralkanoyl anhydride from the thus formed product, treating the product with strong mineral acid and then treating the acid solution with an alkali metal hydroxide or ammonium hydroxide to yield the desired product.

In accordance with the present invention, an appropriate anilide such as 3'-acetylacetanilide, 3'-acetylformanilide, 3'-acetylpropionanilide or 3'-acetylbutyranilide is dissolved in an inert solvent such as methylene chloride, chloroform, carbon tetrachloride or the like, and treated with bromine, chlorine, or the like, to form the corresponding 3'-chloro or 3'-bromoacetylacetanilide, formanilide, propionanilide, or butyranilide shown as formula (I) on the flow diagram hereinafter.

Treatment of the formula (I) anilide with an equimolar amount of 2-aminothiazole or 2-amino-2-thiazoline in an inert solvent such as methylene chloride, chloroform, acetone, ethyl acetate or the like, at a temperature between about 20°C. and 75°C., yields the 3'-[(2-imino-4-thiazolin-3-yl)acetyl]acetanilide, formanilide, propionanilide, or butyranilide, hydrochloride or hydrobromide salt of formula (II). This salt is treated with at least the theoretical amount of an alkali metal borohydride in the presence of a lower alcohol such as methanol, ethanol, butanol, isopropanol, water-lower alcohol mixture or the like and then acidified with an organic or hydrohalide mineral acid to form the hydroxyethyl acetanilide hydrohalide of formula (IVB). We have also found that the formula (II) iminothiazolinyl anilide hydrohalide can be treated with acetic anhydride in the presence of an inert solvent such as acetic acid and an alkali metal acetate at a temperature between about 50°C. and 120°C. to obtain the formula (III) 2-acetylimino thiazolinyl anilide readily converted to the thiazolinyl anilide formula (IVA) by reaction with an alkali metal borohydride. The reaction conditions used are similar to the alkalimetal borohydride treatment of the formula (II) compounds.

Cyclization of the thiazolinyl anilide (IVA) and hydrohalide (formula IVB) can be carried out by reacting said compounds with thionyl chloride at a temperature between 40°C. and 75°C. and treating the reaction product with acetic anhydride at about 50°C. to 140°C. The reaction product is then dissolved in hydrochloric acid and made basic with ammonium hydroxide or an alkali metal hydroxide to yield the dihydroimidazo thiazolyl acetanilide shown as formula (V). If this product is then treated with perchloric acid, the perchlorate salt of formula (V) is obtained.

Cyclization of the formula (IV) compounds can also be achieved by reaction with concentrated sulfuric acid. The free base is obtained by treatment of the reaction product with strong base such as ammonium hydroxide or alkali metal hydroxide. This reaction yields both the dihydro and the tetrahydroimidazo thiazolyl acetanilide free bases of formula (V). Treatment of the imidazo thiazolyl acetanilide of formula (V) with hydrochloric or hydrobromic acid yields the aminophenyl imidazothiazole dihydrohalide of formula (VII).

Advantageously, the formula (VII) compound can also be prepared from 2,3,5,6-tetrahydro-6-(m-nitrophenyl)imidazo[2,1-b]thiazole hydrochloride (VI) by reacting such compound with stannous chloride and hydrochloric acid at higher temperature, for example, between about 60° and 100°C. The resulting product is then neutralized with an alkali metal hydroxide separated from the tin salts and the reduced product treated with an alcoholic hydrohalide.

The m-aminophenyl compound of formula (VII) as the free base can be converted to the corresponding formanilide of formula (VIII), by reaction with formic acid. The reaction may be carried out in the presence of an inert solvent such as toluene, or in formic acid alone. The reaction is generally carried out at a temperature between 50°C. and 125°C. but 75°C. to 100°C. is usually a preferred range.

The formanilide (VIII) is then treated with lithium aluminum hydride in the presence of an inert solvent such as tetrahydrofuran at a temperature between about 25°C. and 75°C. and preferably 40°C. to 50°C. The m-methylaminophenyl imidazothiazole of formula (IX) is then obtained.

Also, in accordance with the present invention, 1-6-(m-aminophenyl)-2,3,5,6-tetrahydroimidazol[2,1-b]thiazole dihydrochloride is obtained by resolution of racemic dl-2,3,5,6-tetrahydro-6-(m-nitrophenyl)imidazo[2,1-b]thiazole with d-tartaric acid to give the l-base, d-tartrate salt which is converted to the free base and then to 1-6-(m-nitrophenyl)-2,3,5,6-tetrahydroimidazo[2,1-b]thiazole hydrochloride. Reduction of 1-6-(m-nitrophenyl)-2,3,5,6-tetrahydroimidazo[2,1-b]thiazole hydrochloride with stannous chloride in hydrochloric acid gives the desired 1-6-(m-aminophenyl)-2,3,5,6-tetrahydroimidazo[2,1-b]thiazole dihydrochloride useful as an intermediate in the present invention. This reaction is illustrated as follows:

VI

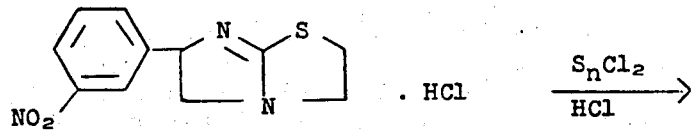

1-6-(m-nitrophenyl)-2,3,5,6-tetrahydroimidazo[2,1-b]thiazole hydrochloride and d-6-(m-nitrophenyl)-2,3,5,6-tetrahydroimidazo[2,1-b]thiazole hydrochloride.

VII

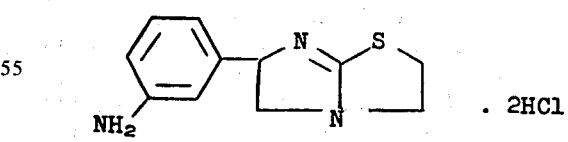

1-6-(m-aminophenyl)-2,3,5,6-tetrahydroimidazo[2,1-b]thiazole dihydrochloride and d-6-(m-aminophenyl)-2,3,5,6-tetrahydroimidazo[2,1-b]thiazole dihydrochloride.

The reactions described above can be illustrated by the following:

FLOW DIAGRAM I
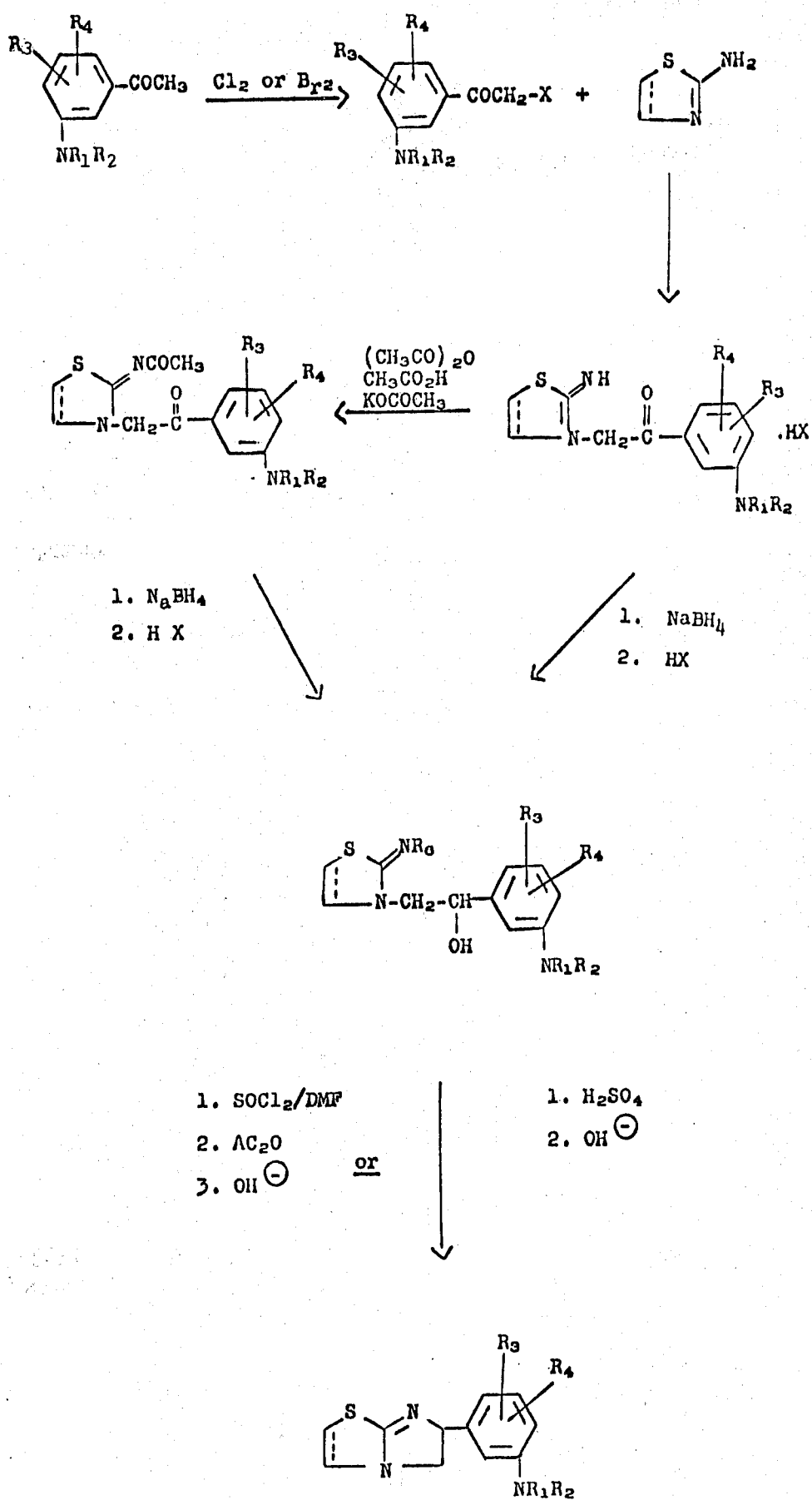

For the preparation of compounds where $R_1$ is hydrogen and $R_2$ is $-COR_5$, process steps are similar to those shown above and are illustrated in Flow Diagram II, as follows:
FLOW DIAGRAM II
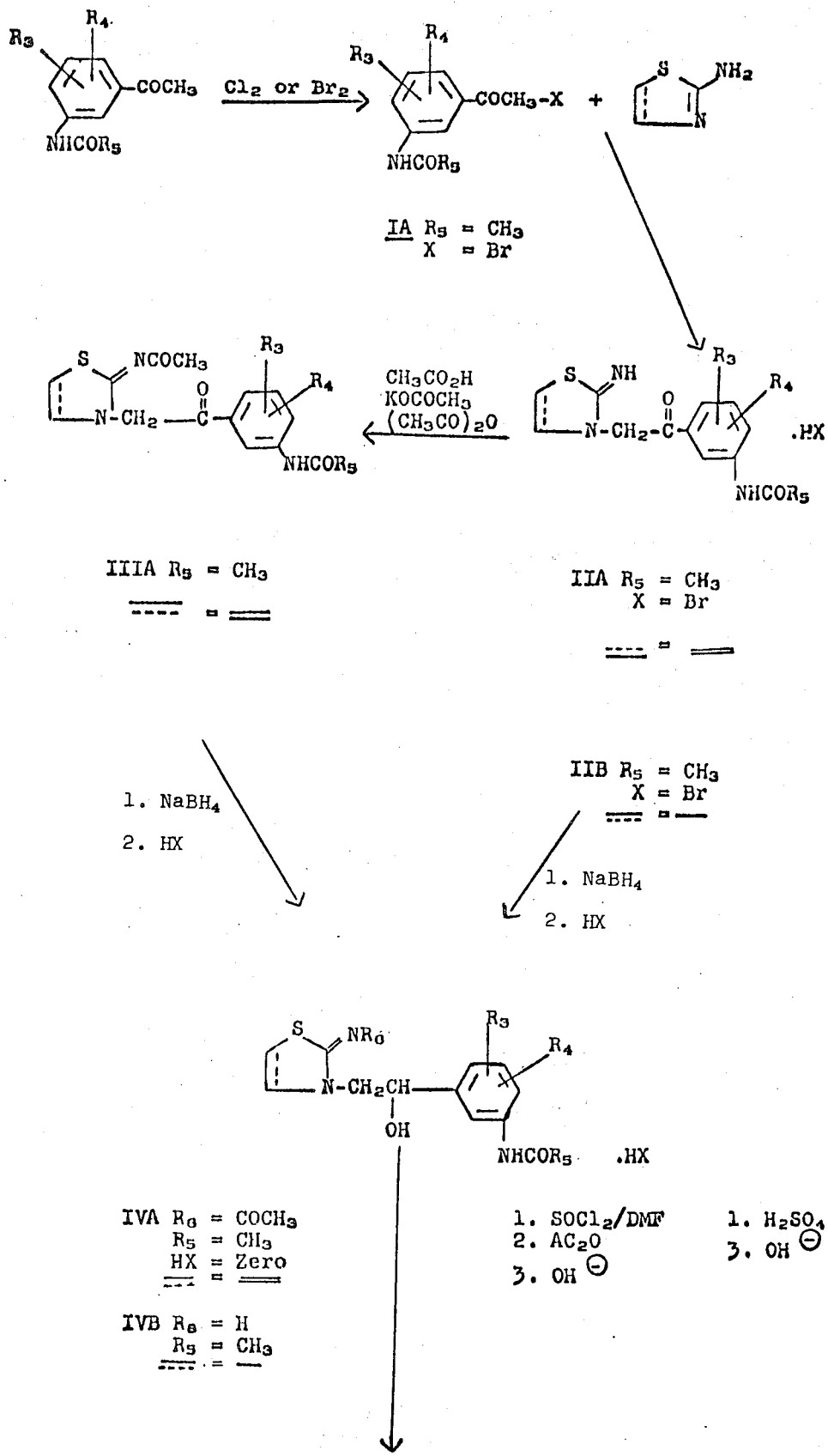

FLOW DIAGRAM II -continued
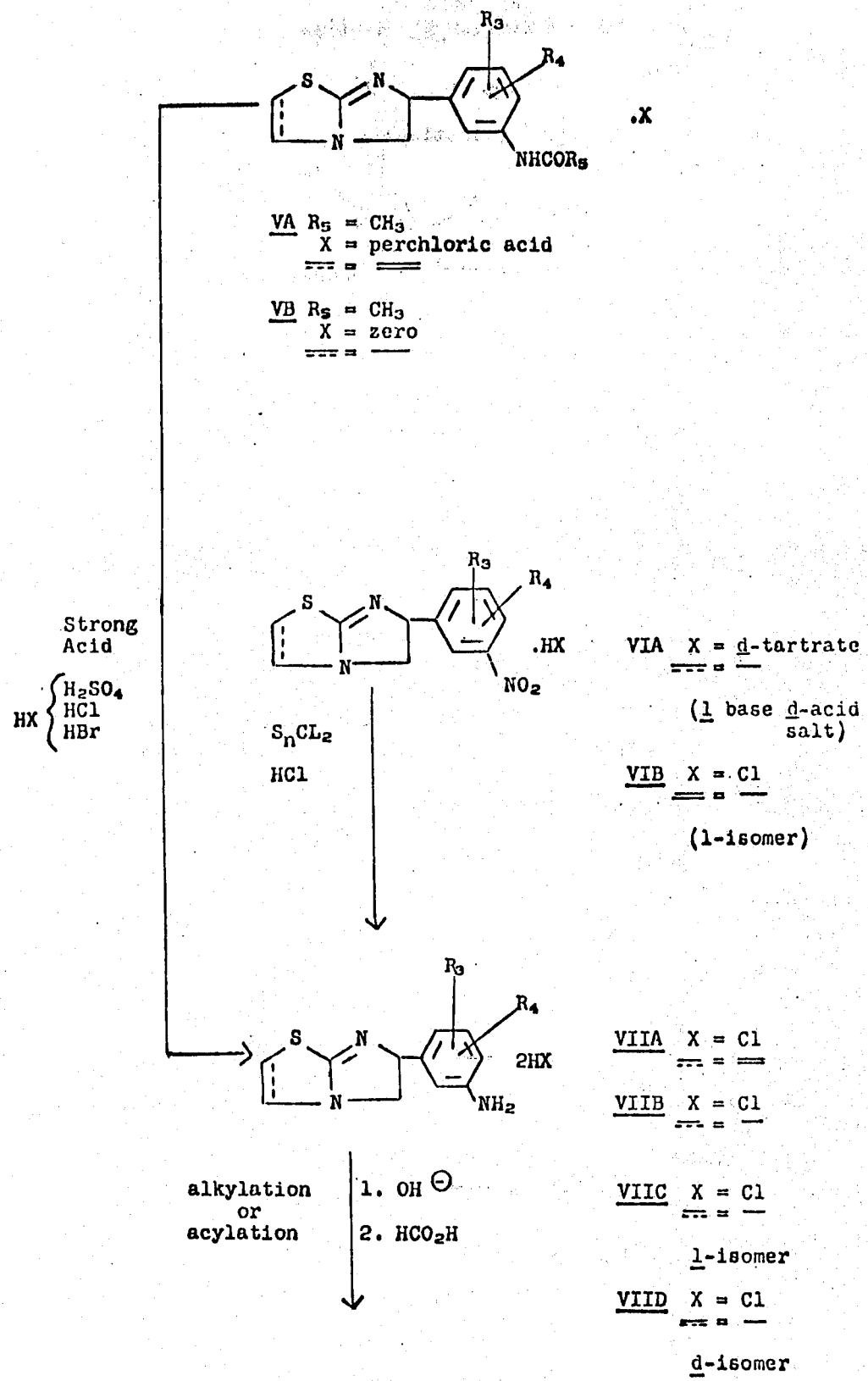

FLOW DIAGRAM II - continued
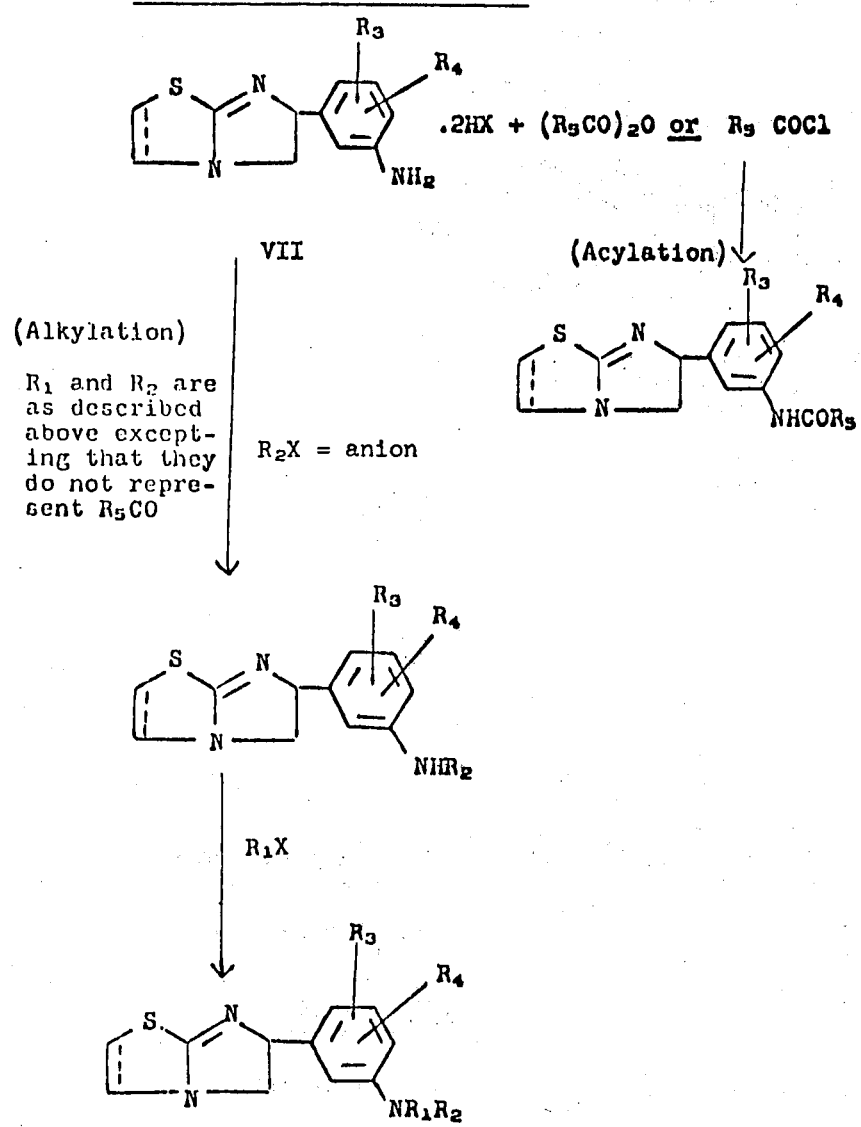
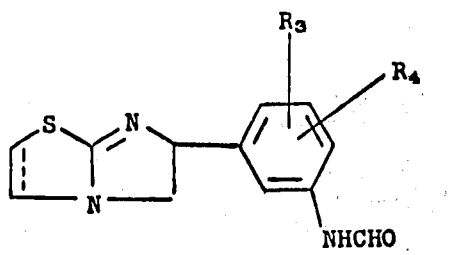
1. LiAlH$_4$
2. HX
VIIIA
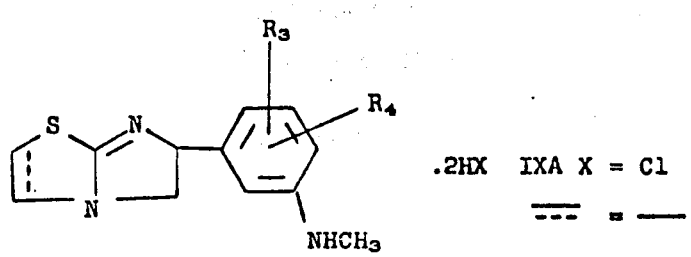
.2HX  IXA  X = Cl wherein $R_6$ is hydrogen or acetyl, $R_5$ is hydrogen or lower alkyl ($C_1$–$C_3$), X is perchlorate, chlorine or bromine and ⇌ is a single or double bond.

The compounds at the present invention can also be prepared using as starting material 6-(m-aminophenyl)-2,3,5,6-tetrahydroimidazo[2,1-b]thiazole. The dl-(m-acylaminophenyl)-2,3,5,6-tetrahydro[2,1-b]thiazoles can be resolved into the d and l isomers with the optically active dibenzoyltartaric acids. The acetamido, isobutryamido, and benzamido derivatives are especially easily resolved with this reagent. The amide group is then removed by acid hydrolysis. The l-isomer of the m-aminophenyl compound is almost twice as active as the dl compound and can be used in the same manner as an intermediate. The m-aminophenyl compound can be acylated or alkylated to produce the desired compounds. The reactions can be carried out at a temperature of from 20°C. to 120°C. usually in the presence of a solvent.

The alkylamino compounds are best prepared by reductive alkylation procedures as illustrated by the equation below:

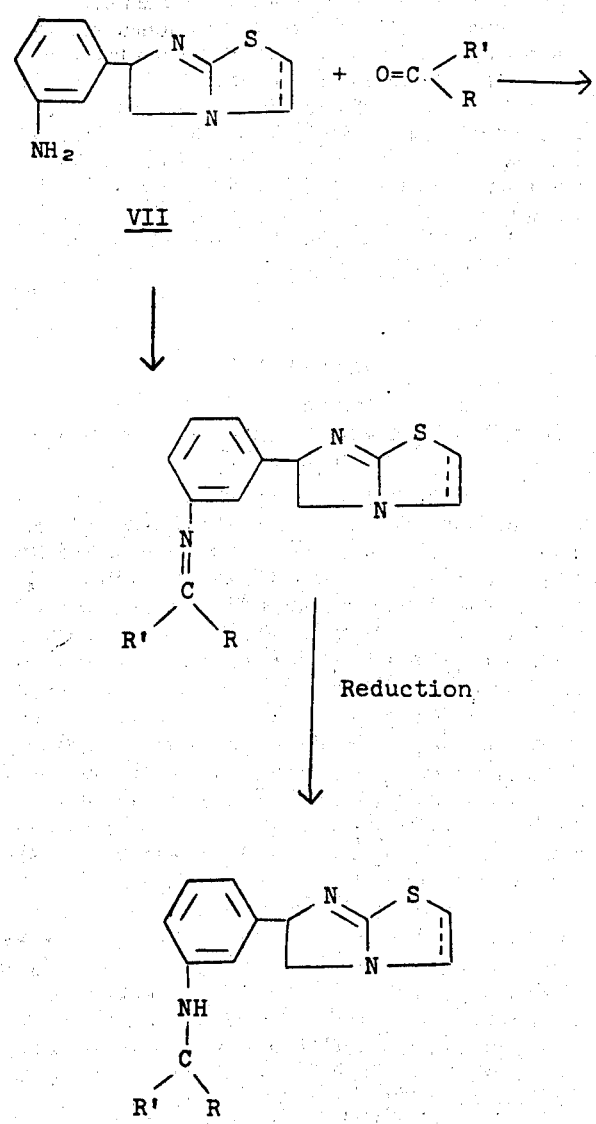

wherein R and R' are hydrogen, alkyl or aryl.

This method is especially useful for aldehyde carbonyl compounds since the reduction proceeds very rapidly and in high yield. Furthermore, there is no alkylation at the 7-position of the imidazo[2,1-b]thiazole ring system. The preferred reagent for preforming the reduction is sodium cyanoborohydride although other reagents can be used under certain conditions.

These products are also available by direct alkylation of the amine compounds (VII) with alkyl halides. This method is useful for secondary halides since they do not alkylate the 7-position readily.

The compounds of the present invention are useful as anthelmintic agents effective for treating helminthiasis in warm-blooded animals.

They are highly effective at very low dosage levels, for example, at from 1 to about 10 mg./kg. of body weight and preferably are utilized at dose levels from 1.5 to 5.0 mg./kg. of body weight of warm-blooded animal. Importantly, they are effective for removing all of the important gastrointestinal nematodes; namely, ascarids, hookworm, whipworms and tapeworms. They have the advantage over their known relatives of being highly effective against whipworms, a helminth heretofore extremely difficult to control. They may be used for treatment of helminthiasis in laboratory, farm and domestic animals as well as wild animals held in captivity and are particularly useful in the treatment of helminthiasis inn Canidae.

Advantageously, the active compounds may be administered orally or parenterally. They may be administered orally in the form of a tablet, pill, capsule, bolus, which may vary from 50 mg. to 10 grams, or as a drench, liquid formulation or in the feed. When used parenterally, the compound is generally dissolved in a pharmaceutically acceptable carrier such as distilled water, polyethyleneglycol or the like and adjusted to a pH between 3.5 to 6.5 and given by subcutaneous or intramuscular injection.

DETAILED DESCRIPTION

The following examples describe in detail the preparation of compounds of this invention and the testing of representative compounds against helminths in warm-blooded animals.

EXAMPLE 1

Preparation of 3'-Bromacetylacetanilide (IA)

To a stirred solution of 110.0 g. (0.62 mole) of 3'-acetylacetanilide in 2400 ml. of chloroform is added dropwise a solution of 33.0 ml. (102.9 g; 0.644 mole) of bromine in 240 ml. of chloroform. The solution is stirred one hour and the resultant precipitate is then filtered, washed with ether and dried. The solid is stirred in a large volume of water to give an oily precipitate which crystallizes on further stirring. The solid is filtered, washed with water and then 2-propanol. The dried product weighs 148.34 g., and is recrystallized from 2-propanol to give the product, melting point 108.5°–110°C. Analysis: Calcd. for $C_{10}H_{10}BrNO_2$:

Calcd: C, 46.90; H, 3.94; Br, 31.20; N, 5.47. Found: C, 47.12; H, 3.94; Br, 31.21; N, 5.47.

EXAMPLE 2

Preparation of 3'-[(2-Imino-4-thiazolin-3-yl)acetyl]acetanilide hydrobromide (IIA)

A solution of 64.8 g. (0.253 mole) of 3'-bromoacetyl acetanilide (Example 1) and 25.3 g. (0.253 mole) of 2-aminothiazole in 450 ml. of acetone is heated at 50°–60°C. for two hours. The precipitated product is filtered, washed with acetone and dried to give 58.74 g. of crude product which on recrystallization from methanol-ether gives the product melting point 225° dec. Anal. Calcd. for $C_{13}H_{14}BrH_3O_2S$: C, 43.83; H, 3.96; Br, 22.43; N, 11.80; S, 9.00. Found: C, 43.90; H, 4.21; Br, 22.21; N, 11.73; S, 8.69.

EXAMPLE 3

Preparation of 3'-[(2-Imino-3-thiazolidinyl)acetyl]acetanilide hydrobromide (IIB)

A solution of 5.12 g. (0.020 mole) of 3'-bromoacetylacetanilide in 70 ml. of acetone is added to a stirred solution of 2.04 g. (0.020 mole) of 2-amino-2-thiazoline in 30 ml. of acetone. The mixture is stirred 1.5 hours and the precipitate then filtered, washed with acetone and dried to give 6.00 g. of white solid, which on recrystallization from water gives the product, melting point 275°–277°C. Anal. Calcd. for $C_{13}H_{16}BrN_3O_2S$: C, 43.58; H, 4.50; Br, 22.31; N, 11.73; S, 8.95. Found: C, 43.99; H, 4.66; Br, 22.51; N, 11.72; S, 9.14.

EXAMPLE 4

Preparation of 3'-[2-(acetylimino)-4-thiazolin-3-yl]acetyl acetanilide (IIIA)

A mixture of 35.6 g. (0.10 mole) of 3'-[2-imino-4-thiazolin-3-yl)acetyl]acetanilide hydrobromide, (Example 2) 11.8 g. (0.12 mole) of potassium acetate, 150 ml. of acetic anhydride and 150 ml. of acetic acid is stirred at reflux for one hour. The mixture is cooled to 50°C., filtered, and the filtrate evaporated at reduced pressure. The residue is azeotroped with toluene, then triturated with 2-propanol and filtered to give 25.8 g. of crude product, which on recrystallization from aqueous acetic acid gives the product, melting point 224°–226°C. Anal. Calcd. for $C_{15}H_{15}N_3O_3S$: C, 56.77; H, 4.76; N, 13.24; S, 10.10. Found: C, 56.88; H, 4.77; N, 13.16; S, 9.90.

EXAMPLE 5

Preparation of 3'-2-[2-(acetylimino)-4-thiazolin-3-yl]-1-hydroxyethylacetanilide hydrobromide (IVA)

To a stirred mixture of 3.2 g. (0.01 mole) of 3'-[2-(acetylimino)-4-thiazolin-3-yl]acetyl acetanilide (Example 4) in 30 ml. of 95% ethanol is added 0.30 g. (0.0078 mole) of sodium borohydride. The mixture is stirred 2.5 hours, poured into water and acidified with acetic acid. The solution is evaporated under reduced pressure and the residue crystallized from dilute hydrobromic acid to give 2.25 g. of product, which on recrystallization from water gives the product, melting point 228°C., dec. Anal. Calcd. for $C_{15}H_{18}BrN_3O_3S$: C, 45.00; H, 4.53; Br, 19.96; N, 10.50; S, 8.01. Found: C, 45.11; H, 4.81; Br, 20.16; N, 10.57; S, 7.74.

EXAMPLE 6

Preparation of 3'-[1-Hydroxy-2-(2-imino-3-thiazolidinyl)ethyl]acetanilide hydrochloride (IVB)

To a stirred slurry of 63.47 g. (0.177 mole) of 3'-[(2-imino-3-thiazolidinyl)acetyl]acetanilide hydrobromide (Example 3) in 1 liter of 95% ethanol, maintained at 5°C., is added 5.70 g. (0.15 mole) of sodium borohydride. After stirring 40 minutes an additional 4.10 g. of sodium borohydride is added and the mixture is acidified with hydrochloric acid and evaporated under reduced pressure. The residue is partitioned between chloroform and dilute aqueous ammonium hydroxide. Two further chloroform extracts are combined with the original, washed with brine, dried (sodium sulfate) and evaporated to give an oil. Treatment with acetone gives 26.77 g. (48%) of white crystalline hydrochloride, which has melting point 235°–237°C. Anal: Calcd. for $C_{13}H_{18}ClN_3O_2S$:x Calcd: C, 49.44; H, 5.74; Cl, 11.23; N, 13.31; S, 10.15. found: C, 49.87; H, 5.27; Cl, 11.51; N, 13.25; S, 10.40.

EXAMPLE 7

Preparation of 3'-(5,6-Dihydroimidazo[2,1-b]thiazol-6-yl)acetanilide perchlorate (VA)

To a stirred mixture of 6.00 g. (0.015 mole) of 3'-2-[2-(acetylimino)-4-thiazolin-3-yl]-1-hydroxyethyl acetanilide hydrobromide (Example 5) in 90 ml. of dry DMF (dimethylformamide) is added dropwise, 2.0 g. (0.017 mole) of thionyl chloride. The mixture is stirred two hours at 50°–55°C. then cooled to 25°C. and stirred while 1.17 g. (0.0099 mole) of thionyl chloride is added dropwise. The mixture is stirred 30 minutes at 25°C. and then at 50°–55°C. for one hour. The mixture is cooled, filtered, and the filtrate evaporated at reduced pressure. After refluxing the residue is 100 ml. of acetic anhydride for 1.5 hours, the acetic anhydride is distilled at reduced pressure. The residue is dissolved in dilute hydrochloric acid, filtered, made basic with conc. ammonium hydroxide and extracted twice with methylene chloride. The combined organic layers are extracted with dilute hydrochloric acid and the product extracted with base back into methylene chloride. The dried methylene chloride solution is evaporated to give an oil which is converted to the perchlorate salt, which on recrystallization from 95% ethanol gives the product, melting point 185°–187°C. Analysis: Calcd. for $C_{13}H_{14}ClN_3O_5S$: Calcd: C, 43.39; H, 3.92; Cl, 9.85; N, 11.68; S, 8.91. Found: C, 43.37; H, 3.82; Cl, 9.90; N, 11.50; S, 8.82.

EXAMPLE 8

Preparation of
3'-(2,3,5,6-Tetrahydroimidazo[2,1-b]thiazol-6-yl)acetanilide (VB)

Addition of 5.00 g. (0.0158 mole) of 3'-[1-hydroxy-2-(2-imino-3-thiazolidinyl)ethyl]acetanilide hydrochloride (Example 6) to 15 ml. of concentrated sulfuric acid is carried out in small increments over 0.5 hour. The orange solution is stirred an additional 1 hour, poured onto ice and made basic with concentrated ammonium hydroxide. The aqueous base is extracted twice with chloroform and the combined organic layers washed with water, brine, dried (sodium sulfate) and evaporated at reduced pressure to give 3.76 g. of an oil. Crystallization from ether gives 3.32 g. (80% crude yield) of fine white crystals, which on recrystallization from 2-propanol gives the product melting point 164°–166°C. Analysis: Calcd. for $C_{13}H_{15}N_3OS$: Calcd: C, 59.74; H, 5.79; N, 16.08; S, 12.27. Found: C, 59.93; H, 5.85; N, 15.96; S, 12.49.

EXAMPLE 9

Preparation of
6-(m-Aminophenyl)-5,6-dihydroimidazo[2,1-b]thiazole dihydrochloride (VIIA)

A 2.80 g. (0.0078 mole) portion of 3'-(5,6-dihydroimidazo[2,1-b]thiazol-6-yl)acetanilide perchlorate (Example 7) is converted to the free base and then dissolved in 15 ml. of 6N hydrochloric acid. The solution is stirred at reflux for 1.6 hours and then evaporated at reduced pressure. The residue is azeotroped with 2-propanol and crystallized from 95% ethanol/-2-propanol to give 1.69 g. (75%) of crystalline product, melting point 242°–244°C. Anal. Calcd. for $C_{11}H_{13}Cl_2N_3S$: C, 45.54; H, 4.52; Cl, 24.43; N, 14.48; S, 11.05. Found: C, 45.39; H, 4.66; Cl, 24.26; N, 12.27; S, 10.83.

EXAMPLE 10

Preparation of
6-(m-Aminophenyl)-2,3,5,6-tetrahydroimidazo[2,1-b]thiazole Dihydrochloride (VIIB)

A solution of 1.00 g. (0.0038 mole) of 3'-(2,3,5,6-tetrahydroimidazo[2,1-b]thiazol-6-yl)acetanilide (Example 8) in 17 ml. of 6N hydrochloric acid is heated at reflux for 2.5 hours and then allowed to stand overnight at room temperature. The solution is concentrated at reduced pressure, made basic with concentrated aqueous sodium hydroxide while cooling and then extracted with 3 portions of chloroform. The combined organic layers are washed with brine, dried (sodium sulfate) and evaporated to give 0.84 g. of an oil, i.e., m-aminotetramisole free base. The oil is dissolved in hot methanol and strongly acidified with hydrogen chloride in 2-propanol. Evaporation of the solution and crystallization of the residue from 2-propanol gives 0.91 g. (81%) of cream colored solid, melting point 198°–201°C., dec.

EXAMPLE 11

Preparation of
6-(m-Aminophenyl)-2,3,5,6-tetrahydroimidazo[2,1-b]thiazole Dihydrochloride (VIIB)

To a stirred slurry of 22.57 g. (0.10 mole) of stannous chloride dihydrate in 35 ml. of conc. hydrochloric acid, cooled to 5°C. is added 7.14 g. (0.025 mole) of 6-(m-nitrophenyl)2,3,5,6-tetrahydroimidazo[2,1-b]thiazole hydrochloride in one portion. The reaction is allowed to proceed to 40°C. for 30 minutes and then heated to 75°–80°C. for 3 hours. After pouring onto ice, the mixture is neutralized with aqueous sodium hydroxide and extracted into methylene chloride. The methylene chloride solution is washed with water, dried (magnesium sulfate) and evaporated at reduced pressure to give the free base as a yellow oil. The free base is dissolved in methanol and treated with excess 2-propanol-hydrogen chloride. Evaporation of the solvent and treatment of the oil residue with acetonitrile gives 5.08 g. (68% yield) of crude product which is recrystallized from 95% ethanol to give the white product, melting point 202°–205°C. Anal. Calcd. for $C_{11}H_{15}N_3SCl_2$: C, 45.21; H, 5.17; N, 14.38; S, 10.97; Cl, 24.27. Found: C, 44.80; H, 5.60; N, 14.08; S, 11.07; Cl, 24.07.

EXAMPLE 12

Preparation of
3'-(2,3,5,6-Tetrahydroimidazo[2,1-b-]thiazol-6-yl)-formanilide (VIIIA)

Method A
A mixture of 3.29 g. (0.015 mole) of 6-(m-aminophenyl)-2,3,5,6-tetrahydroimidazo[2,1-b]thiazole free base, (obtained by basification of the dihydrochloride salt), 5 g. of 90% formic acid and 45 ml. of toluene is stirred in an oil bath while maintaining a very slow distillation. The initial distillate containing water distilled at 76°–92°C. The temperature rises to 105°C. After two more distillations with 45 ml. of toluene and 5 g. of 90% formic acid, the total reaction is 4 hours. The residue is partitioned between aqueous potassium carbonate and chloroform. The aqueous layer is extracted with chloroform and the combined organic layers washed with water, dried (magnesium sulfate), and the solvent evaporated at reduced pressure to give a white solid. Trituration with acetonitrile and recrystallization from ethanol gives the product, melting point 177°–179°C.

Method B
A solution of 14.5 g. (0.0664 mole) of the free base is dissolved in 75 ml. of 97–100% formic acid and the solution heated in the steam bath 2 hours. The excess formic acid is distilled on a rotary evaporator at reduced pressure. The syrupy residue is dissolved in water. Some methylene chloride and cracked ice is added and the two-phase system stirred and basified with potassium carbonate solution. The bulk of the product crystallizes and is insoluble in either phase. This fraction is recovered by filtration, washed with water followed by acetonitrile. A small amount is obtained by evaporation of the dried (potassium carbonate) methylene chloride phase bringing the total yield to 11.15 g. (0.045 mole), 60%; melting point 176°–178°C.

EXAMPLE 13

Preparation of
2,3,5,6-Tetrahydro-6-(m-methylaminophenyl-)imidazo[2,1-b]thiazole Dihydrochloride (IXA)

To a stirred slurry of 1.15 g. (0.030 mole) of lithium aluminum hydride in 80 ml. of dry tetrahydrofuran is added 5.00 g. (0.0203 mole) of 3'-(2,3,5,6-tetrahydroimidazo[2,1-b]thiazol-6-yl)formanilide (Example 12) at a rate sufficient to keep the temperature at 40°–45°C. The reaction mixture is then stirred at room temperature for 3 hours and at 40°–50°C. for 30 minutes. After cooling the reaction, 1.8 ml. of water is cautiously added dropwise and then 2 ml. of 15% aqueous sodium hydroxide. The mixture is filtered and the filter cake washed with tetrahydrofuran. Evaporation of the solvent gives an oil which is dissolved in methanol and acidified with 2-propanolic hydrogen chloride. Filtration of the precipitate gives 4.18 g. (67% yield) of crude product which is recrystallized from methanol and has melting point 229°–231°C. Anal. Calcd. for $C_{12}H_{16}N_3SCl$: C, 47.06; H, 5.60; N, 13.72; S, 10.47; Cl, 23.15. Found: C, 46.82; H, 5.56; N, 13.60; S, 10.40; Cl, 23.16.

EXAMPLE 14

Preparation of
1-2,3,5,6-Tetrahydro-6-(m-nitrophenyl)imidazo[2,1-b]thiazole d-tartrate (VIA)

Procedure A

A 28.58 g. (0.10 mole) portion of the dl-6-(m-nitrophenyl)-2,3,5,6-tetrahydroimidazo[2,1-b]thiazole hydrochloride is converted to the free base. A mixture of the free base, 15.0 1 g (0.10 mole) of d-tartaric acid in 520 ml. of 95% ethanol is heated on thee steam bath and then allowed to cool to 30°C. The precipitated salt is filtered, washed with ethanol and dried to give 15.4 g. (77%) of the l-base, d-acid salt, melting point 181°–182°C., dec., $[\alpha]_d$–58.1° (C 7.7, $H_2O$). Two recrystallizations from 90% ethanol give the analytical sample, melting point 182°C., dec., $[\alpha]_d$–60.3° (c 7.5, $H_2O$).

Procedure B

To a solution of 0.05 mole of d,1-6-(m-nitrophenyl)-2,3,5,6-tetrahydroimidazo[2,1-b]thiazole free base (prepared from 14.30 g. (0.050 mole) of the corresponding hydrochloride) in 200 ml. of hot ethanol was added 3.75 g. (0.025 mole) of d-tartaric acid in one portion. The mixture is refluxed briefly and then allowed to cool to room temperature. The precipitate is filtered, washed with absolute ethanol and dried to give 7.95 g. (79.7%) of the l-base, d-acid salt, melting point 184°C., $[\alpha]_d$–56.2° (c 6.8, $H_2O$).

EXAMPLE 15

Isolation of
1-6-(m-Nitrophenyl)-2,3,5,6-tetrahydroimidazo[2,1-b]thiazole hydrochloride (VIB)

Conversion of 10.4 g. of l-base, d-tartrate salt to the free base and treatment of an ethanolic solution of the free base with 2-propanol-hydrogen chloride gives 7.05 g. of l-6-(m-nitrophenyl)-2,3,5,6-tetrahydroimidazo[2,1-b]thiazole hydrochloride, melting point 209°–210°C., $[\alpha]_d = -96.9°$ (c 6.7, $H_2O$). Two recrystallizations from ethanol gives the essentially pure product with $[\alpha]_d$ –99.4° (c 6.4, $H_2O$).

EXAMPLE 16

Preparation of
l-6-(m-Aminophenyl)-2,3,5,6-tetrahydroimidazo[2,1-b]thiazole Dihydrochloride (VIIC)

The procedure described for the reduction of dl-6-(m-nitrophenyl)-2,3,5,6-tetrahydroimidazo[2,1-b]thiazole hydrochloride (Example 11) is followed. From 14.98 g. (0.0524 mole) of l-2,3,5,6-tetrahydro-6-(m-nitrophenyl)imidazo[2,1-b]thiazole hydrochloride (Example 15) is obtained 11.03 g. of the product free base as an oil. The free base is dissolved in methanol and acidified with 2-propanol-hydrogen chloride to give 9.97 g. (68% yield) of white crystalline product, melting point 273°–276°C., $[\alpha]_D^{25}$ – 78.5° (c 10, $H_2O$). The analytical sample, melting point 276.5°–279°C., id obtained from water/2-propanol. Anal. Calcd. for $C_{11}H_{15}N_3SCl_2$: C, 45.21; H, 5.17; N, 14.38; S, 10.97; Cl, 24.27. Found: C, 45.23; H, 5.19; N, 14.34; S, 11.08; Cl, 24.17.

EXAMPLE 17

Preparation of
d-2,3,5,6-Tetrahydro-6-(m-aminophenyl)imidazo[2,1-b]thiazole Dihydrochloride (VIID)

The procedure described in Example 16 is followed. From 14.00 g. (0.0491 mole) of d-6-(m-nitrophenyl)-2,3,5,6-tetrahydroimidazo[2,1-b]thiazole hydrochloride (obtained from dl-6-(m-nitrophenyl-2,3,5,6-tetrahydroimidazo[2,1-b]thiazole and l-tartaric acid) is obtained 12.75 g. (89%) recrystallized d-6-(m-aminophenyl)-2,3,5,6-tetrahydroimidazo[2,1-b]thiazole dihydrochloride, melting point 277°–278°C., $[\alpha]_D^{25}$ + 84.6° (c 9.9, $H_2O$). Anal. Found: C, 45.39; H, 5.21; N, 14.47; S, 11.19.

EXAMPLE 18

Preparation of
l(–)6-(m-Isobutrylaminophenyl)-2,3,5,6-tetrahydroimidazo[2,1-b]thiazole dibenzoyl l-(+) tartrate A solution of 2.9 g. (0.01 mole) of 6-m-isobutrylaminophenyl)-2,3,5,6-tetrahydroimidazo[2,1-b]thiazole in 15 ml. of hot methanol is added to a solution of 3.8 g. (0.1 mole) of dibenzoyl-d-tartaric acid in 25 ml. methanol. The salt which crylstallizes on cooling is recovered by filtration. The yield is 2.7 g. 83% of the l(–) amine, melting point 183.5°–184.5°C. Recrystallization gives a product melting point 182°–183°C. $[\alpha]_D^{25}$ = –75.6° (C=1.37 dimethylsulfoxide).

The other isomer of the amine is obtained by employing the other optically active dibenzoyl tartaric acid.

EXAMPLE 19

Using the same procedure described in the Example 18 above, the acetamide and benzamido analogs are resolved. These resolved salts can be acid hydrolyzed to obtain the amino derivative by methods well known for hydrolyzing amides. They can also be converted to the base form of the imidazo[2,1-b]thiazole by treatment of the tartrate salts with ammonium hydroxide or other base. The physical properties of some of the resolved salts are listed in the table below.

TABLE I

Dibenzoyl-d-tartrate salts

| R | Melting Point Degree C. | Solvent of Re-cryst. | Specific Rotation $(\alpha)_D^{25}$ | Empirical Formula | % Calculated C | H | N | S | % Found C | H | N | S |
|---|---|---|---|---|---|---|---|---|---|---|---|---|
| NH—COCH₃ | 153.5–154.5 | MeOH | −125.0 (C=1.60, MeOH) | $N_3SOC_{13}H_{15}\cdot O_8C_{18}H_{19}$ | 60.09 | 4.72 | 6.78 | 5.18 | 59.45 | 4.76 | 7.38 | 5.74 |
| NH—COCH(CH₃)₂ | 182–183° | MeOH | −75.6° (C=1.37 DMSO) | $N_3SOC_{15}H_{19}\cdot O_8C_{18}H_{19}$ | 61.19 | 5.14 | 6.49 | 4.95 | 60.77 | 5.18 | 6.54 | 5.03 |
| NH—CO—⟨phenyl⟩ | 204–207° | — | −70.6° (C=0.90, DMSO) | $N_3SOC_{18}H_{17}\cdot O_8C_{18}H_{19}$ | 63.42 | 4.58 | 6.16 | 4.70 | 63.25 | 4.63 | 6.65 | 5.15 |

EXAMPLE 20

Preparation of 6-(m-isopropylaminophenyl)-2,3,5,6-tetrahydroimidazo[2,1-b]thiazole 5.0 g. (0.023 mole) of the free base of imidazo[2,1-b]thiazole 2,3,5,6-tetrahydro-6-(m-aminophenyl)dihydrochloride (m-aminotetramisole) is dissolved in a mixture of 40 ml. of methanol and 20 ml. of 1 N sodium acetate water solution. The pH of the solution is adjusted to 6-7 (slightly acid) with addition of acetic acid (2 ml.) and the solution is then added to 8.5 g. (0.05 mole) of 2-iodopropane. The mixture is refluxed for 48 hours. After cooling, the excess 2-iodopropane and methanol is evaporated on the rotary evaporator. The residue is then partitioned between 100 ml. chloroform and 50 ml. water. With stirring and cooling, the system is made basic (pH 10) by the addition of sodium hydroxide solution. The chloroform layer is removed, and the aqueous layer is washed with (2 × 75 ml. portions) of chloroform. The chloroform extracts are dried over magnesium sulfate and the chloroform evaporated to yield a white solid, melting point 47°–51°C. The isopropylated product is then dissolved in 150 ml. acetone and a solution of hydrogen chloride-acetone is added. The hydrochloride salt as an acetone solvate precipitates from the solution. The salt is filtered to yield 2.2 g. (0.056 mole, 25% yield) of a white solid, melting point 80°–170°C. Calcd. C, 42.83; H, 5.40; N, 10.71; S, 8.17; Cl, 18.07. Found: C, 43.78; 43.89; H, 5.55; 5.79; N, 10.85; S, 8.47; Cl, 18.29.

EXAMPLE 21

Preparation of 6-[m-(isopropylmethylamino)phenyl]-2,3,5,6-tetrahydroimidazo[2,1-b]thiazole The above compound is prepared in a manner similar to Example 1 by alkylating 3'-N-methyl-m-aminotetramisole with 2-iodopropane in a water-methanol solution. The product which is very hydroscopic has infrared and nmr spectra consistent with what was expected for the product.

EXAMPLE 22

Preparation of N-isopropyl-3'-(2,3,5,6-tetrahydroimidazo[2,1-b]thiazol-6-yl) formanilide dihydrochloride To 4.0 g. (0.015 mole) of the 3'-N-isopropyl-m-aminotetramisole derivative, Example 18, is added 25 ml. of formylacetic anhydride. The mixture is heated on a steam bath overnight (14 hours). The excess anhydride is then removed under reduced pressure and the residue is taken up in 50 ml. of chloroform. The chloroform solution is washed (3 × 75 ml.) with water. The water washings are combined and 100 ml. chloroform is added. The mixture is made basic (pH 10) with sodium hydroxide solution and the chloroform layer separated. The aqueous layer is extracted with 2 × 100 ml. portions of additional chloroform. The chloroform extracts are combined, dried over magnesium sulfate and the solvent removed under reduced pressure to yield 2.6 g. of a thick oil. The formylated product is purified by column chromatography (silica gel, chloroform and 10% methanol/CHCl₃ used as elutants). The hydrochloride salt is prepared by dissolving the free base in chloroform and bubbling in gaseous hydrogen chloride. The salt did not precipitate and therefore the salt is isolated by removing the chloroform under reduced pressure. The crystalline, white solid, melting point 55°–70°C. is found to be very hygroscopic. Calcd. C, 47.37; H, 6.10; N, 11.04; S, 8.43; Cl, 18.64. Found: C, 47.76; H, 4.98; N, 10.68; S, 8.14; Cl, 17.32.

EXAMPLE 23

Preparation of 3'-(2,3,5,6-tetrahydroimidazo[2,1-b]thiazol-6-yl)isobutyranilide hydrochloride 2.2 G. (0.010 mole) of m-aminotetramisole is dissolved in a mixture of 15 ml. methanol and 15 ml. water and the pH is adjusted to about 6 with an aqueous hydrochloric acid solution. This solution is then added to 3.2 g. (0.020 mole) of isobutyric anhydride. The mixture is allowed to stand at room temperature for 12 hours. The reaction mixture is then added to a mixture of 100 ml. methylene chloride and 50 ml. water and then made basic (pH 10) with an aqueous sodium hydroxide. The methylene chloride layer is removed and the water layer is washed twice with 75 ml. of fresh methylene chloride. The methylene chloride extracts are then combined, dried over magnesium sulfate, and the methylene chloride evaporated leaving a tacky solid. The free base of the product is recrystallized from a chloromethyl ether mixture. The yield is 1.6 g. (55%). The hydrochloride salt is prepared by dissolving the free base in methanol and adding an excess of hydrogen chloride gas. The methanol is then removed on the rotary evaporator to yield a glassy white solid, melting point 125°–140°C. Calcd. C, 52.39; H, 6.45; N, 12.22; S, 9.32; Cl, 10.31. Found: C, 52.40; H, 6.25; N, 12.32; S, 9.46; Cl, 10.57.

EXAMPLES 24–30

Following the procedure of Example 21 and reacting dl- or l-meta-aminotetramisole with the proper acid chloride or anhydride, compounds of the following structure are obtained.

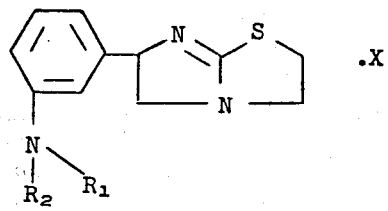

EXAMPLES 31–32

Preparation of
3'-(5,6-Dihydroimidazo[2,1-b]thiazol-6-yl)pivalanilide and
3'-(5,6-dihydroimidazo[2,1-b]-6-yl)-isobutyranilide To a stirred solution of 2.0 g. (0.007 mole) of 6-(m-aminophenyl)-5,6-dihydroimidazo[2,1-b]thiazole dihydrochloride in 50 ml. of 50% aqueous methanol is added aqueous sodium hydroxide to give pH 5–6. Pivalic anhydride is added and the solution is stirred overnight at room temperature. Chloroform is added and the pH is adjusted to 9–10 with aqueous sodium hydroxide. The organic layer is separated and evaporated to dryness. The residue is slurried with ether and filtered to given 1.6 g. crude product. Recrystallization from ethyl acetate gives 0.75 g. of 3'-(5,6-dihydroimidazo[2,1-b]thiazol-6-yl)pivalanilide, melting point 163°–165°C.

By the above procedure 3'(5,6-dihydroimidazo[2,1-b]thiazol-6-yl)isobutyranilide, melting point 175°–178°C. is obtained when isobutyric anhydride is used in place of pivalic anhydride.

EXAMPLE 33

Preparation of
dl-m-(2,3,5,6-tetrahydroimidazo[2,1-b]thiazol-6-yl)carbanilic acid methyl ester, hydrochloride To 2.6 g. (0.009 mole) of the dihydrochloride of dl-m-aminotetramisole (Example 10) is added 40 ml. of a 1.0 m-sodium acetate buffer. The solution (pH = 4.6) is cooled in an ice bath and then 3.0 g. (0.032 mole) of methyl chloroformate is added, (2 molar excess) and the solution stirred for 15 minutes. After an

| $NR_1R_2$ | X | Melting point | Melting point free base | Analysis calculated | | Analysis found | |
|---|---|---|---|---|---|---|---|
| HN—CO—CH$_2$CH$_3$ dl  24 | HCl H$_2$O Solvate | 120–130 | 120–122 | C H N S S Cl | 50.97 6.11 12.74 9.72 9.72 10.75 | C H N S S Cl | 51.02 6.02 12.96 9.68 9.68 10.98 |
| HN—CO—CH$_2$CH$_2$CH$_3$ dl  25 | HCl H$_2$O Solvate | 112–122 | 92–93 | C H N S Cl | 52.39 6.45 12.22 9.32 10.31 | C H N S Cl | 52.44 6.37 12.36 9.21 10.41 |
| HN—CO—CH(CH$_3$)$_2$ dl  26 | HCl H$_2$O Solvate | 110–130 | — | — | | — | |
| HN—CO—C(CH$_3$)$_3$ dl  27 | HCl H$_2$O Solvate | 145–160 | 109–111 | C H N S Cl | 53.67 6.76 11.74 8.96 — | C H N S Cl | 54.33 6.59 12.59 9.65 — |
| HN—CO—C(CH$_3$)$_3$ l  28 | HCl H$_2$O Solvate | 140–155 | — | — | | — | |
| HN—CO—CH(CH$_2$CH$_3$)$_2$ dl  29 | HCl H$_2$O Solvate | 120–135 | 65–73 | C H N S Cl | 54.89 7.05 11.30 8.62 9.53 | C H N S Cl | 54.82 7.03 11.21 8.68 9.59 |
| HN—CO—C$_6$H$_5$ dl  30 | HCl H$_2$O Solvate | 128–140 | 94–100 | C H N S Cl | 57.21 5.33 11.12 8.49 9.38 | C H N S Cl | 57.81  57.98 5.03 10.92 8.05 9.30 | additional 15 minutes at room temperature, the solution is then cooled in an ice bath and 50 ml. methylene chloride is added. The mixture is made basic with an aqueous sodium hydroxide solution (pH 10).

The methylene chloride layer is separated and the water washed (2 × 50 ml.) with additional methylene chloride. The methylene chloride washings are combined, dried over magnesium sulfate and on removal of the solvent, 1.4 g. (50% crude yield) of product as the free base is isolated. After being recrystallized from ethyl acetate the free base has a melting point of 135°–138°C. The free base is converted to the hydrochloride salt by dissolving the recrystallized free base in acetone and passing dry hydrogen chloride gas through the solution. The hydrochloride salt precipitates and is recrystallized from ethanol; melting point 245°–246°C. Anal. C, 49.75; H, 5.14; N, 13.39; S, 10.22; Cl, 11.30. Found: C, 49.72; H, 5.30; N, 13.10; S, 9.93; Cl, 11.02.

EXAMPLE 34

Preparation of l-m-(2,3,5,6-tetrahydroimidazo[2,1-b]thiazol-6-yl)carbanilic acid methyl ester, hydrochloride Following the procedure of Example 33 and substituting l-m-aminotetramisole for dl-m-aminotetramisole the above compound is obtained having a melting point of 239°–240°C. The analysis of the compound is as follows: Anal. C, 49.75; H, 5.14; N, 13.39; S, 10.22; Cl, 11.30. Found: C, 49.65; H, 5.21; N, 13.20; S, 10.05; Cl, 11.40.

EXAMPLE 35

Preparation of l-6-(5-amino-2-nitrophenyl)-2,3,5,6-tetrahydroimidazo[2,1-b]thiazole, hydrochloride, acetone solvate 4.3 g. (0.014 mole) of the nitrate salt of 1-N-acetyl-m-aminotetramisole is cooled in an acetone-dry ice bath and then 50 ml. of concentrated sulfuric acid is added. The salt dissolves in the sulfuric acid and the solution is allowed to stand at room temperature for five days. The mixture is then poured over 200 g. of ice and 300 ml. of chloroform is added. With cooling in an acetone-dry ice bath, the acid is neutralized with concentrated ammonium hydroxide and the pH is adjusted to about 10. The chloroform layer is separated and the water layer washed with an additional 150 ml. chloroform. The chloroform extracts are combined, washed with water, dried over magnesium sulfate and the solvent evaporated on a rotary evaporator to yield 3.3 g. of a yellow solid. The yellow solid is then heated in 50 ml. 6 N hydrochloric acid in a steam bath for 3 hours in order to hydrolyze the acetyl group. After cooling, 200 ml. chloroform is added and the acid neutralized with concentrated ammonium hydroxide. The pH is adjusted to 10 and the chloroform layer removed. The water layer is washed twice with an additional 100 ml. chloroform. Then the chloroform washings are combined, dried over magnesium sulfate, and the solvent removed to yield 1.5 g. of a yellow solid. The nitro compound is recrystallized from chloroform and dried; melting point 228°–229°C. (dec.). The free base is converted to the hydrochloride salt by dissolving the free base in acetone and then a saturated hydrogen chlorideacetone solution is added. The hydrochloride salt precipitates out and is filtered and dried; melting point 140°–210°C. The salts could not be readily recrystallized. Anal. C, 46.74; H, 5.21; N, 15.58; S, 8.92; Cl, 9.86. Found: C, 45.20; H, 4.99; N, 15.68; S, 9.08; Cl, 11.79.

EXAMPLE 36

Preparation of dl-6-(4-bromo-3-nitrophenyl)-2,3,5,6-tetrahydroimidazo[2,1-b]thiazole, hydrochloride On the nitration of 4-bromotetramisole (6-(4-bromophenyl)-2,3,5,6-tetrahydroimidazo[2,1-b]thiazole) recovering the nitrated product as the free base and acidifying with hydrogen chloride, the above compound is obtained having a melting point of 227°–229°C. Analysis Calcd. for: C, 36.23; H, 3.04; N, 11.53; S, 8.79; Br, 21.92. Found: C, 35.97; H, 2.96, N, 11.40; S, 8.52; Br, 22.09.

On reduction of the above nitro compound the corresponding amino compound (6-(3-amino-4-bromophenyl)-2,3,5,6-tetrahydroimidazo[2,1-b]thiazole) is obtained as the free base having a melting point of 129°–130°C.

EXAMPLE 37

Preparation of dl-6-(5-amino-2-bromophenyl)-2,3,5,6-tetrahydroimidazo[2,1-b]thiazole, dihydrochloride To 3.3 g. (0.015 mole) of dl m-amino tetramisole is added 40 ml. of concentrated sulfuric acid along with 2.5 g. silver sulfate. The mixture is warmed on the steam bath to get the solids in solution. Then 2.7 g. (0.017 mole) of bromine is added slowly to the warm solution and there is an immediate formation of a white precipitate. The reaction mixture is stirred at room temperature for 12 hours and then is poured over about 100 g. of ice. The silver bromide precipitate is filtered off, the sulfuric acid solution is cooled in an ice bath, 150 ml. of chloroform is added, and the acidic solution is then carefully neutralized with concentrated ammonium hydroxide. The pH is raised to about 10, the chloroform layer is separated, and the water layer washed twice with an additional 75 ml. chloroform. The chloroform washings are dried over magnesium sulfate and the solvent removed on the rotary evaporator to yield an off-white solid, which is recrystallized from chloroform. The brominated product has a melting point of 153°–156°C. The hydrochloride salt is prepared by dissolving the free base in acetone and adding hydrogen chloride gas. The white salt precipitates out and is filtered and dried; 2.6 g. (47% yield). The salt is recrystallized from ethanol and dried; melting point 170°–210°C. (dec.). Calcd. C, 35.60; H, 4.02; N, 11.32; S, 8.64. Found: C, 36.94; H, 4.02; N, 10.75; S, 8.17.

EXAMPLE 38

Preparation of l-6-(5-acetylamino-2-bromophenyl)-2,3,5,6-tetrahydroimidazo[2,1-b]thiazole Following the procedure of Example 35 and substituting l-acetylaminotetramisole for dl-m-aminotetramisole the above compound is obtained having as the base a melting point of 195°–197°C. On analysis the product had the following values: C, 45.89; H, 4.15; N, 12.35; S, 9.43; Br, 23.49; Found: C, 46.15; H, 3.85; N, 12.50; S, 9.45; Br, 23.82.

EXAMPLE 39

Preparation of 1-6-(5-amino-2-bromophenyl)-2,3,5,6-tetrahydroimidazo[2,1-b]thiazole Following the procedure of Example 35 and substituting l-m-aminotetramisole for dl-m-aminotetramisole the above product is obtained having a melting point of 175°–177°C. An analytical sample on analysis shows calculated C, 44.30; H, 4.06; N, 14.04; S, 10.75; Br, 26.80. Found: C, 44.10; H, 4.02; N, 13.96; S, 10.75; Br, 26.58.

EXAMPLES 40–46

General method for acylation of 6-(m-aminophenyl)-2,3,5,6-tetrahydroimidazo[2,1-b]thiazole and 6-(m-aminophenyl)-5,6-dihydroimidazo[2,1-b]thiazole to prepare the amide or the carbamate function A solution of the amino derivative in an aqueous system is treated with at least one molar equivalent of a carboxylic acid halide or anhydride or alkoxycarbamoyl chloride at a pH suitable for amide formation at the amino group but not favorable for acylation at the 7-nitrogen in the imidazo ring. After the anhydride or chloride has reacted the reaction mixture is made basic which preferentially hydrolyzes only acyl groups from the 7-position leaving only the desired compounds. Details for specific compounds are listed in Examples 21, 28, 29, 30, 31 and 32. Using these procedures the following are prepared.

| Starting Material | Acylating Agent Chloride or Anhydride | Product |
|---|---|---|
| (structure with NH$_2$) | | (structure with R) |
| 40 | CH$_3$(CH$_2$)$_n$CO— | R=CH$_3$(CH$_2$)$_n$CNH— (n=1 to 9) |
| 41 | X—⟨⟩—CO— (with Y) | R=X—⟨⟩—CONH— (with Y) (Y and x=H, lower alkyl and halogen) |
| 42 | CH$_2$—CH—CO— \(CH$_2$)$_n$ | R=CH$_2$—CH—C—NH— \(CH$_2$)$_n$ (n=1 to 5) |
| 43 | Olefinic- H C=C=C— | R=—C=C—C—NH— (H) |
| 44 | X—⟨⟩—(CH$_2$)$_n$CO— (with Y) | X—⟨⟩—(CH$_2$)$_n$—CONH— (with Y) (N=1 to 6) (X and Y=H, halogen, loweralkyl) |
| 45 | Heterocyclic- C— | Heterocyclic —C—N—H Heterocyclic = pyridyl, thiazolyl, furfuryl, etc. |
| 46 | Alkoxy—C— | Alkoxy- C—N—H (C$_1$ to C$_8$) |

EXAMPLES 47–52

The following is a general method for alkylating 6-(m-aminophenyl)-2,3,5,6-tetrahydroimidazo[2,1-b]thiazole and 6-(m-aminophenyl-5 6-dihydroimidazo[2,1-b]thiazole. The procedure outlined in Example 18 is used to prepare other 6-(alkylaminophenyl)-5,6-dihydro and 2,3,5,6-tetrahydroimidazo[2,1-b]thiazoles. Preparations of these compounds are outlined below.

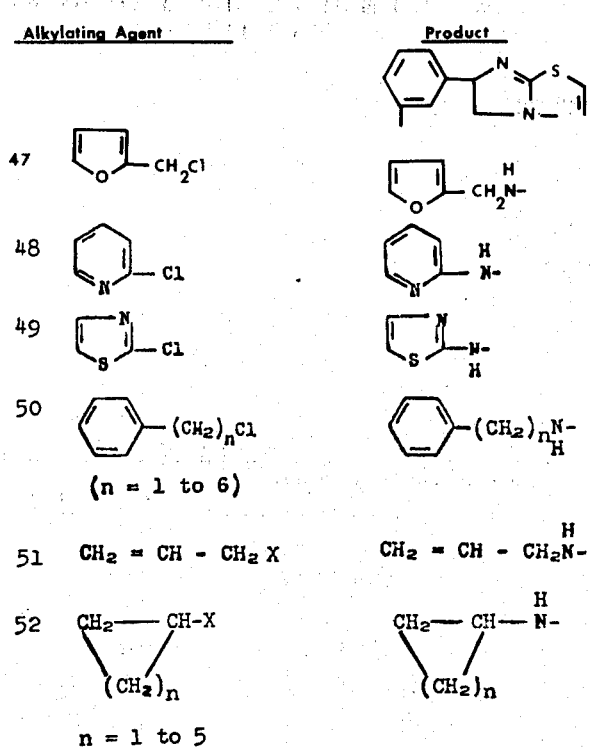

EXAMPLE 53

Preparation of 6-[m-(Furfurylamino)phenyl]-2,3,5,6-tetrahydroimidazo[2,1-b]thiazole A mixture of 4.4 g. (0.020 mole) of 6-(m-aminophenyl)-2,3,5,6-tetrahydroimidazo[2,1-b]thiazole, 2.1 g. (0.022 mole) furfural, 3.5 ml. acetic acid and 50 ml. methanol are placed in a reaction flask along with some molecular sieves. To this 0.63 g. (0.01 mole) of sodium cyanoborohydride is added slowly and the mixture stirred two hours. The mixture is now acidified to pH 1 with hydrochloric acid. A solid material is removed by trituration and the solvent evaporated leaving an oily residue.

The oil is partitioned between dilute HCl and chloroform. The aqueous layer is separated and fresh chloroform is added. The two phase mixture is made alkaline with ammonium hydroxide and the chloroform layer separated, dried and evaporated. The oily product crystallizes from ether to yield 4.1 g. (69%). The product has a melting point 99.5°–101°C. after recrystallization from an ethyl acetate-heptane mixture. Anal. Calcd. for $C_{16}H_{17}N_3SO$: C, 64.19; H, 5.72; N, 14.03; S, 10.71. Found: C, 64.47; H, 5.67; N, 14.20; S, 11.04.

EXAMPLE 54

Following the procedure outlined in the previous Example 53 and substituting the appropriate aldehyde or ketone, the following compounds are prepared:

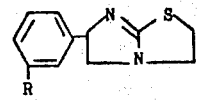

| R | % Yield | Melting Point | Solvent of Recryst. | Empirical Formula | % Calculated C | H | N | S | % Found C | H | N | S |
|---|---|---|---|---|---|---|---|---|---|---|---|---|
| HN—CH(CH₃)—CH₂OH | 27 | 165–170° | CH₂Cl₂ | $N_3SOC_{14}H_{19}$ | 60.62 | 6.90 | 15.15 | 11.56 | 60.41 | 6.74 | 14.89 | 11.37 |
| HN—(cyclohexyl) | 43 | 157–160° | EtOAc-heptane | $N_3SC_{17}H_{23}$ | 67.74 | 7.69 | 13.94 | 10.64 | 68.00 | 7.66 | 14.08 | 10.59 |
| HN—CH₂-(furyl) | 69 | 99.5–101° | EtOAc-heptane | $N_3SOC_{16}H_{17}$ | 64.19 | 5.72 | 14.03 | 10.71 | 64.47 | 5.67 | 14.20 | 11.04 |
| HN—CH₂-(phenyl) | 48 | 114–116° | EtOAc-heptane | $N_3SC_{18}H_{19}$ | 69.87 | 6.19 | 13.58 | 10.36 | 70.09 | 5.63 | 13.43 | 10.70 |
| HN—CH₂-(C₆H₄)-OCH₃ | 60 | 114–118° | EtOAc-heptane | $N_3SOC_{19}H_{21}$ | 67.23 | 6.24 | 12.38 | 9.44 | 67.10 | 6.29 | 12.50 | 9.56 |
| HN—CH₂-(pyridyl) | 65 | 107–110° | EtOAc-heptane | $N_4SC_{17}H_{18}$ | 65.78 | 5.84 | 18.05 | 10.33 | 65.70 | 5.80 | 18.26 | 10.29 |

EXAMPLES 55–112

The following are two general methods which are used for preparing the 6-(substituted phenyl)-2,3,5,6-tetrahydroimidazo[2,1-b]thiazoles and 6-(substituted phenyl)-5,6-dihydroimidazo[2,1-b]thiazoles shown in Table II.

A. Following the procedures outlined in Examples 1, 2, 3, 4, 5, 6, 7 and 8, a series of substituted compounds are prepared from substituted acetopheneones which are prepared by the procedures described in the chemical literature. Compounds prepared by this procedure are illustrated below:

In the case where

represents a basic function, that is a primary, secondary or tertiary amine, the starting aminoacetopheneone is utilized as its hydrochloride or hydrobromide salt in the Example 1 reaction with bromine to form the aα-bromoacetylaniline.

B. Following the procedures outlined in Examples 20, 21, 23, 31, 32 and 33, dl- or l-m-aminotetramisole is either alkylated with the appropriate alkyl, aralkyl, or heterocyclicalkyl halide or acylated with the appropriate acid chloride or acid anhydride.

Starting Material

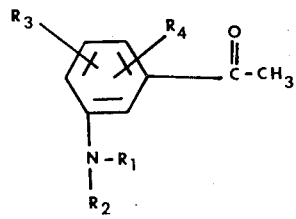

Final Product

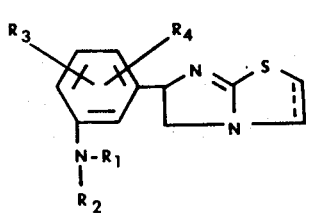

TABLE II

| | Starting Material and Final Product | | |
|---|---|---|---|
| $R_1$ | $R_2$ | $R_3$ | $R_4$ |
| 55 $CH_3$ | —COCH($CH_3$)$_2$ | H | H |
| 56 H | —COCH($CH_3$)$_2$ | —$NO_2$(5) | H |
| 57 H | H | H | Br(6) |
| 58 4-pyridyl | —CO—$CH_3$ | H | H |
| 59 2-thiazoyl | —CO—$CH_3$ | H | H |
| 60 (piperidinyl)N– | | H | H |
| 61 (pyrrolidinyl)N– | | H | H |
| 62 (morpholinyl)N– | | H | H |
| 63 $C_8H_{17}$OCO— | H | H | H |
| 64 $CH_3OCH_2CH_2$— | $(CH_3)_2$CH— | H | H |
| 65 (pyrrolidinyl)NCH$_2$CO— | H | H | H |
| 66 $CH_2$=CH—$CH_2$— | H | Cl(4) | H |

TABLE II-continued

Starting Material and Final Product

| | R₁ | R₂ | R₃ | R₄ |
|---|---|---|---|---|
| 67 | cyclohexyl- | H | H | H |
| 68 | C₆H₅CH₂- | H | H | Cl(6) |
| 69 | (CH₃)₂CH- | (CH₃)₂CHC(O)- | H | H |
| 70 | CH₂=CHCH₂- | CH₂=CH-CH₂- | H | H |
| 71 | C₆H₄(CH)(CH₂-) | H | NO₂(5) | H |
| 72 | CH₃(CH₂)₁₀- | H | H | H |
| 73 | cyclopropyl-CH- | H | H | Cl(6) |
| 74 | H | OHCH₂CH₂- | H | H |
| 75 | C₃H₇-n | C₃H₇-n | H | H |
| 76 | CH₂=CH-CH₂- | CH₂=CH-CH₂- | H | H |
| 77 | C₂H₅C(O)- | H | Cl(4) | H |
| 78 | H₂C=CH-C(O)- | CH₃ | H | H |
| 79 | cyclobutyl-C(O)- | H | H | H |
| 80 | ClCH₂CH₂CH₂C(O)- | H | H | H |
| 81 | C₆H₅-C(O)- | H | H | H |
| 82 | H | piperidinyl-N-C(O)- | H | H |
| 83 | H | pyrrolidinyl-N-C(O)- | H | —NO₂(6) |
| 84 | H | morpholinyl-N-C(O)- | H | H |
| 85 | H | pyridinyl-N-CH₂- | H | H |
| 86 | CH₃-C₆H₄-CH₂- | H | H | H |

TABLE II-continued

| R₁ | Starting Material and Final Product R₂ | R₃ | R₄ |
|---|---|---|---|
| 87 2,4-dimethylphenyl | H | H | H |
| 88 2,3-dimethyl-6-methylphenyl (trimethyl) | H | H | H |
| 89 3-methoxybenzyl | H | H | H |
| 90 3,4-dimethoxyphenyl | H | H | H |
| 91 2,3,5-trimethoxybenzyl | H | H | H |
| 92 benzyl | benzyl | H | H |
| 93 phenethyl (PhCH₂CH₂–) | H | H | H |
| 94 3,4-dichlorobenzyl | H | H | H |
| 95 4-nitrophenethyl (O₂N–C₆H₄–CH₂CH₂–) | H | —NO₂(4) | H |
| 96 2,3,6-tribromobenzyl | H | H | H |
| 97 3,4-dinitrophenyl | H | H | H |

TABLE II-continued

| R₁ | Starting Material and Final Product R₂ | R₃ | R₄ |
|---|---|---|---|
| 98  $O_2N-\langle\phantom{x}\rangle-$ | H | H | $-NO_2(6)$ |
| 99  4-pyrimidinyl | H | H | H |
| 100  H | 2-pyrimidinyl | H | H |
| 101  H | furfuryl ($\langle O \rangle-CH_2-$) | H | H |
| 102  H | $C_2H_5NHC(O)-$ | H | H |
| 103  $(CH_3)_2NHCH_2C(O)-$ | H | H | H |
| 104  $CH_3CH(OCH_3)CH_2C(O)-$ | H | H | H |
| 105  $(CH_3)_2NHC(O)-$ | H | H | H |
| 106  2-naphthoyl | H | H | H |
| 107  $(CH_3)_2NCH=$ | | H | H |
| 108  $CH_3NHC(O)-$ | H | H | H |
| 109  $H_2NC(O)-$ | H | H | H |
| 110  H | tetrahydrofurfuryl ($\langle O \rangle-CH_2-$) | H | H |
| 111  H | $\langle O \rangle-CH_2-C(O)-$ (tetrahydrofuryl) | H | H |
| 112  H | $\langle O \rangle-CH_2-C(O)-$ (furyl) | H | H |

EXAMPLE 113

Preparation of Imidazo[2,1-b]thiazole, 6-(m-dimethylaminophenyl)-2,3,5,6-tetrahydrodihydrochloride A quantity of 6.0 g. (50 mmol) of thionyl chloride is slowly added to 6.0 g. (18 mmol) of 3'-[1-hydroxy-2-(2-imino-3-thiazolidinyl)ethyl]dimethylanilide hydrochloride in 100 ml. chloroform and the reaction mixture is stirred for one hour at room temperature. Then 200 ml. of water is added to the reaction mixture and the pH of the solution is adjusted to 9–10 with potassium carbonate. The two phase system is refluxed for 8 hours. The chloroform layer is separated, dried over magnesium sulfate and on removal of the solvent, 2.2 g. of a dark oil is isolated. The free base is then dissolved on acetone, acidified with hydrogen chloride and the product precipitated out. The dihydrochloride salt is filtered and dried. Yield 1.3 g. Melting point 170°–200°C. The product could not be purified by recrystallization from the usual sllvents. Structure is based on a comparison of IR and NMR spectra of the compound to closely related compounds.

EXAMPLES 114–173

Following the procedures hereinbefore described the 6-(meta-aminophenyl)-1,2,3,4-tetrahydro and 5,6-dihydroimidazo[2,1-b]thiazoles are prepared and identified.

TABLE III

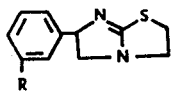

| Example | R | Melting Point | Solvent of Recryst. | Empirical Formula |
|---|---|---|---|---|
| 114 | NH—CH(CH$_3$)—CH$_2$OH | 165–170° | CH$_2$Cl$_2$ | N$_3$SOC-H$_{19}$ |
| 115 | HN—⬡ | 157–160° | EtOAc - heptane | N$_3$SC$_{17}$H$_{23}$ |
| 116 | HN-CH$_2$-(furan) | 99.5–101° | EtOAc - heptane | N$_3$SOC$_{16}$H$_{17}$ |
| 117 | HN-CH$_2$-⬡ | 114–116° | EtOAc - heptane | N$_3$SC$_{18}$H$_{19}$ |
| 118 | HN-CH$_2$-⬡-OCH$_3$ | 114–118° | EtOAc - heptane | N$_3$SOC$_{19}$H$_{21}$ |
| 119 | HN-CH$_2$-(pyridyl) | 107–110° | EtOAc - heptane | N$_4$SC$_{17}$H$_{18}$ |
| 120 | CH$_3$—N—CH(CH$_3$)$_2$ | — | — | N$_3$SC$_{15}$H$_{21}$ |
| 121 | HN—CO—OCH$_3$ | 137–138° | EtOAc | N$_3$SO$_2$C$_{13}$H$_{15}$ |
| 122 | HN—CO—CH$_2$CH$_3$ | 120–122° | CHCl$_3$—Et$_2$O | N$_3$SOC$_{14}$H$_{17}$ |
| 123 | HN—CO—(CH$_2$)$_2$CH$_3$ | 92.5–94.5 | CHCl$_3$—Et$_2$O | N$_3$SOC$_{15}$H$_{19}$ |
| 124 | HN—CO—CH(CH$_3$)$_2$ | 118–120° | CHCl$_3$— | N$_3$SOC$_{15}$H$_{19}$·H$_2$O |
| 125 | HN—CO—C(CH$_3$)$_3$ | 109–111° | CHCl$_3$—Et$_2$O | N$_3$SOC$_{16}$H$_{21}$·H$_2$O |
| 126 | HN—CO—(CH$_2$)$_3$CH$_3$ | 80–82° | CHCl$_3$—Et$_2$O | N$_3$SOC$_{18}$H$_{25}$·½ H$_2$O |
| 127 | HN-CO-⬡ | 130–132° | CHCl$_3$—Et$_2$O | N$_3$SOC$_{18}$H$_{23}$·H$_2$O |
| 128 | HN-CO-CH$_2$-⬡ | 182–184°(dec.) | CHCl$_3$ Benzene | N$_3$SOC$_{19}$H$_{19}$ |
| 129 | HN-CO-CH=CH-⬡ | 128–130°(dec.) | CHCl$_3$- Benzene | N$_3$SOC$_{20}$H$_{19}$ |
| 130 | HN-CO-CH$_2$Cl | 325° | Acetone | N$_3$SOClC$_{13}$H$_{14}$ |

TABLE III-continued

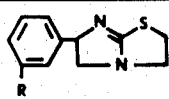

| Example | R | Melting Point | Solvent of Recryst. | Empirical Formula |
|---|---|---|---|---|
| | | | MeOH | |
| 131 | NH₂ I- | 121–122° | Toluene | N₃SC₁₁H₁₃ |
| 132 | HN-CO-C₆H₅ | 101–105° | CHCl₃ | N₃SOC₁₈H₁₇·2H₂O |
| 133 | HN-CO-C₆H₄-Cl | 136–140°(dec.) | CHCl₃—Benzene | N₃SOClC₁₈H₁₆ |
| 134 | HN-CO-C₆H₄-CH₃ | 80–82°(dec.) | CHCl₃—Benzene | N₃SOC₁₉H₁₉·C₆H₆ |
| 135 | HN-CO-C₆H₃-Cl₂ | 150–153°(dec.) | CHCl₃ Benzene | N₃SOCl₂C₁₈H₁₅ |
| 136 | HN-CO-C₆H₄-NO₂ | 174–176°(dec.) | MeOH | N₄SO₃C₁₈H₁₆ |
| 137 | NH-CO-C₆H₄-Cl | 142–144° | CH₂Cl₂ | N₃SOClC₁₈H₁₆ |
| 138 | NH-CO-naphthyl | 209–212°(dec.) | — | N₃SOC₂₂H₁₉ |
| 139 | HN-CO-adamantyl | 150°(dec.) | CHCl₃—Heptane | N₃SOC₂₂H₂₇ |
| 140 | HN—SO₂—CH₃ | 170–173° | EtOAc-Heptane | N₃S₂O₂C₁₂H₁₅ |
| 141 | HN-SO₂-C₆H₅ | 223–224° | Dioxane-H₂O | N₃S₂O₂C₁₇H₁₇ |

| | % Calculated | | | | | % Found | | | | |
|---|---|---|---|---|---|---|---|---|---|---|
| Example | C | H | N | S | Cl | C | H | N | S | Cl |
| 114 | 60.62 | 6.90 | 15.15 | 11.56 | — | 60.41 | 6.74 | 14.89 | 11.37 | — |
| 115 | 67.74 | 7.69 | 13.94 | 10.64 | — | 68.00 | 7.66 | 14.08 | 10.59 | — |
| 116 | 64.19 | 5.72 | 14.03 | 10.71 | — | 64.47 | 5.67 | 14.20 | 11.04 | — |
| 117 | 69.87 | 6.19 | 13.58 | 10.36 | — | 70.09 | 5.63 | 13.43 | 10.70 | — |
| 118 | 67.23 | 6.24 | 12.38 | 9.44 | — | 67.10 | 6.29 | 12.50 | 9.56 | — |
| 119 | 65.78 | 5.84 | 18.05 | 10.33 | — | 65.70 | 5.80 | 18.26 | 10.29 | — |
| 120 | — | — | — | — | — | — | — | — | — | — |
| 121 | 56.30 | 5.45 | 15.15 | 11.56 | — | 56.35 | 5.37 | 15.00 | 11.53 | — |
| 122 | 61.06 | 6.22 | 15.26 | 11.65 | — | 61.23 | 6.20 | 15.28 | 11.62 | — |
| 123 | 62.25 | 6.62 | 14.52 | 11.08 | — | 62.16 | 6.63 | 14.53 | 11.12 | — |
| 124 | 58.60 | 6.89 | 13.67 | 10.43 | — | 59.14 | 6.39 | 13.64 | 10.54 | — |
| 125 | 59.78 | 7.21 | 13.07 | 10.01 | — | 60.06 | 6.54 | 13.20 | 10.11 | — |

TABLE III-continued

| Example | R | | | | | | | | | |
|---|---|---|---|---|---|---|---|---|---|---|
| 126 | 63.49 | 7.70 | 12.34 | 9.42 | — | 63.59 | 7.57 | 12.43 | 9.40 | — |
| 127 | 62.19 | 7.25 | 12.08 | 9.22 | — | 62.15 | 6.46 | 12.20 | 9.34 | — |
| 128 | 67.63 | 5.68 | 12.45 | 9.50 | — | 68.01 | 5.72 | 12.33 | 9.45 | — |
| 129 | 68.74 | 5.48 | 12.02 | 9.18 | — | 69.70 | 5.68 | 11.50 | 8.89 | — |
| 130 | 52.79 | 4.77 | 14.21 | 10.84 | 11.99 | 52.89 | 4.76 | 14.10 | 10.73 | 12.19 |
| 131 | 60.25 | 5.97 | 19.16 | 14.62 | — | 60.30 | 6.01 | 19.15 | 14.63 | — |
| 132 | 58.51 | 6.27 | 11.37 | 8.68 | — | 59.05 | 4.81 | 10.81 | 8.51 | — |
| 133 | 60.41 | 4.51 | 11.74 | 8.96 | 9.91 | 60.28 | 4.53 | 11.82 | 9.04 | 9.87 |
| 134 | 72.28 | 5.89 | 10.22 | 7.86 | — | 72.26 | 6.06 | 10.11 | 7.72 | — |
| 135 | 55.11 | 3.85 | 10.71 | 8.17 | 18.07 | 55.78 | 3.93 | 10.80 | 8.10 | 17.55 |
| 136 | 58.68 | 4.38 | 15.21 | 8.70 | — | 58.90 | 4.39 | 14.99 | 8.82 | — |
| 137 | 60.41 | 4.51 | 11.74 | 8.96 | 9.91 | 60.21 | 4.37 | 11.61 | 9.75 | 9.12 |
| 138 | 70.75 | 5.13 | 11.25 | 8.59 | — | 70.30 | 5.04 | 10.99 | 8.49 | — |
| 139 | 69.25 | 7.13 | 11.01 | 8.40 | — | 70.04 | 7.36 | 10.77 | 8.18 | — |
| 140 | 48.46 | 5.08 | 14.13 | 21.56 | — | 48.52 | 5.11 | 14.07 | 21.80 | — |
| 141 | 56.80 | 4.77 | 11.69 | 17.84 | — | 56.69 | 4.97 | 11.45 | 17.80 | — |

(a)Racemic compounds unless indicated otherwise.

TABLE IV

Substituted m-aminotetramisole salts[a]

| Example | R | X | Melting Point | Spec. Rot. $[\alpha]_D^{25}$ | Empirical Formula |
|---|---|---|---|---|---|
| 142 | HN—CH(CH$_3$)$_2$ | 2HCl Acetone Solvate | 80–170° | — | N$_3$SC$_{14}$H$_{19}$.2HCl |
| 143 | (CH$_3$)$_2$CH—N—CHO | 2HCl H$_2$O Solvate | 55–70° | — | N$_3$SOC$_{15}$H$_{19}$.2HCl |
| 144 | N(CH$_3$)$_2$ | 2HCl | 140–200° | — | N$_3$SC$_{13}$H$_{17}$.2HCl |
| 145 | +N(CH$_3$)$_3$ 1- | I H$_2$O Solvate | 154–155° | −40.1° (c=2.6, MeOH) | N$_4$SC$_{14}$H$_{20}$.I |
| 146 | H—N—CO—OCH$_3$ | HCl | 243–244° | — | N$_3$SO$_2$C$_{13}$H$_{15}$.HCl |
| 147 | H—N—CO—OCH$_3$ 1- | HCl | 239–240° | −112.5° (c=1.3, MeOH) | N$_3$SO$_2$C$_{13}$H$_{15}$.HCl |
| 148 | H—N—CO—O—CH(CH$_3$)$_2$ | HCl | 80–90° | — | N$_3$SO$_2$C$_{14}$H$_{19}$.HCl |
| 149 | H—N—CO—CH$_2$CH$_3$ | HCl H$_2$O Solvate | 120–130° | — | N$_3$SOC$_{14}$H$_{17}$.HCl. |
| 150 | H—N—CO—(CH$_2$)$_2$CH$_3$ | HCl H$_2$O Solvate | 112–122° | — | N$_3$SOC$_{15}$H$_{19}$.HCl |
| 151 | H—N—CO—CH(CH$_3$)$_2$ | HCl H$_2$O Solvate | 125–133° | — | N$_3$SOC$_{15}$H$_{19}$.HCl. |
| 152 | H—N—CO—CH(CH$_3$)$_2$ 1- | HCl H$_2$O Solvate | 110–130° | −114.2° (c=1.6, MeOH) | N$_3$SOC$_{15}$H$_{19}$.HCl. |
| 153 | HN—CO—C(CH$_3$)$_3$ | HCl H$_2$O Solvate | 145–160° | — | N$_3$SOC$_{16}$H$_{21}$.HCl. |
| 154 | HN—CO—C(CH$_3$)$_3$ 1- | HCl | 140–155° | −100.0 (c=2.8, MeOH) | N$_3$SOC$_{16}$H$_{21}$.HCl |
| 155 | HN—CO—CH(CH$_2$CH$_3$)$_2$ | HCl H$_2$O Solvate | 120–135° | — | N$_3$SOC$_{17}$H$_{23}$.HCl.H$_2$ |

TABLE IV-continued

Substituted m-aminotetramisole salts[a]

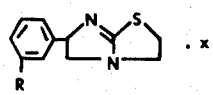

| Example | R | X | Melting Point | Spec. Rot. $[\alpha]_D^{25}$ | Empirical Formula |
|---|---|---|---|---|---|
| 156 | HN—CO(CH$_2$)$_3$CH$_3$ | HCl H$_2$O Solvate | 85–93° | — | N$_3$SOC$_{18}$H$_{25}$·HCl·H$_2$O |
| 157 | HN-CO-cyclohexyl | HCl H$_2$O Solvate | 140–150° | — | N$_3$SOC$_{18}$H$_{23}$·HCl·H$_2$O |
| 158 | HN—CO—CH$_2$C(CH$_3$)$_3$ | HCl H$_2$O Solvate | 142–155° | — | N$_3$SOC$_{17}$H$_{23}$·HCl·H$_2$O |
| 159 | HN-CO-phenyl | HCl H$_2$O Solvate | 128–148° | — | N$_3$SOC$_{18}$H$_{17}$·HCl |
| 160 | HN-CO-phenyl l- | HCl | 258–260° | −113.2° (C=1.4, MeOH) | N$_3$SOC$_{18}$H$_{17}$·HCl |
| 161 | N=CH—N(CH$_3$)$_2$ | 2HCl | 280–282° (dec.) | — | N$_4$SC$_{14}$H$_{18}$·2HCl |
| 162 | HN-CO-C$_6$H$_4$-OCH$_3$ | HCl | 243–245° (dec.) | — | N$_3$SO$_2$C$_{19}$H$_{19}$·HCl |
| 163 | HN-CO-furyl | HCl | 223–225° (dec.) | — | N$_3$SO$_2$C$_{16}$H$_{15}$·HCl |

| | % Calculated | | | | | % Found | | | |
| Example | C | H | N | S | Cl | C | H | H | S | Cl |
|---|---|---|---|---|---|---|---|---|---|---|
| 142 | 42.85 | 5.40 | 10.71 | 8.17 | 18.07 | 43.78 43.89 | 5.55 5.79 | 10.85 | 8.47 | 18.29 |
| 143 | 47.37 | 6.10 | 11.04 | 8.43 | 18.64 | 47.76 | 4.98 | 10.63 | 8.14 | 17.32 |
| 144 | — | — | — | — | — | — | — | — | — | — |
| 145 | 41.28 | 5.45 | 10.32 | 7.87 | I 31.16 | 41.73 | 4.93 | 10.15 | 8.18 | I 31.60 |
| 146 | 49.75 | 5.14 | 13.39 | 10.22 | 11.30 | 49.72 | 5.30 | 13.10 | 9.93 | 11.02 |
| 147 | 49.75 | 5.14 | 13.39 | 10.22 | 11.30 | 49.65 | 5.21 | 13.20 | 10.05 | 11.40 |
| 148 | | | | | | | | | | |
| 149 | 50.97 | 6.11 | 12.74 | 9.72 | 10.75 | 51.02 | 6.02 | 12.96 | 9.68 | 10.93 |
| 150 | 52.39 | 6.45 | 12.22 | 9.32 | 10.31 | 52.44 | 6.37 | 12.36 | 9.21 | 10.41 |
| 151 | 52.39 | 6.45 | 12.22 | 9.32 | 10.31 | 52.40 | 6.25 | 12.32 | 9.46 | 10.57 |
| 152 | 52.39 | 6.45 | 12.22 | 9.32 | 10.31 | 52.28 | 6.42 | 12.26 | 9.52 | 10.66 |
| 153 | 53.67 | 6.76 | 11.74 | 8.96 | — | 54.33 | 6.59 | 12.59 | 9.65 | — |
| 154 | 56.54 | 6.52 | 12.37 | 9.44 | 10.43 | 55.96 | 6.44 | 12.20 | 9.19 | 10.41 |
| 155 | 54.89 | 7.05 | 11.30 | 8.62 | 9.53 | 54.82 | 7.03 | 11.21 | 8.68 | 9.59 |
| 156 | 63.49 | 7.70 | 12.34 | 9.42 | — | 63.59 | 7.57 | 12.43 | 9.40 | — |
| 157 | 56.31 | 6.83 | 10.94 | 8.35 | 9.24 | 55.37 | 6.23 | 11.15 | 8.50 | 10.04 |
| 158 | 54.89 | 7.05 | 11.30 | 8.62 | — | 53.32 | 6.75 | 11.86 | 9.13 | — |
| 159 | 57.21 | 5.33 | 11.12 | 8.49 | 9.38 | 57.81 57.93 | 5.03 | 10.92 | 8.05 | 9.30 |
| 160 | 60.07 | 5.04 | 11.68 | 8.91 | 9.85 | 60.02 | 5.06 | 11.71 | 9.03 | 9.91 |
| 161 | 48.50 | 5.79 | 16.15 | 9.23 | 20.40 | 47.90 | 6.10 | 15.93 | 9.19 | 20.41 |
| 162 | 58.60 | 5.22 | 10.78 | 8.23 | 9.08 | 58.21 | 5.30 | 10.31 | 7.97 | 8.99 |
| 163 | 54.93 | 4.61 | 12.01 | 9.17 | 10.13 | 54.77 | 4.86 | 11.94 | 9.05 | 10.24 |

[a]Racemic compounds unless indicated otherwise.

TABLE V

Disubstituted m-Aminotetramisoles Derivatives[a]

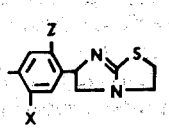

| Example | X | y | Z | X' | Melting Point | Spec. Rot.$[\alpha]_D^{25}$ |
|---|---|---|---|---|---|---|
| 164 | NO$_2$ | Br | H | HCl | 227–229° | — |
| 165 | NH$_2$ | Br | H | — | 129–130.5° | — |

TABLE V-continued

Disubstituted m-Aminotetramisoles Derivatives[a]

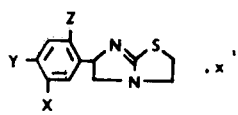

| Example | X | y | Z | X' | Melting Point | Spec. Rot.[α]$_D^{25}$ |
|---|---|---|---|---|---|---|
| 166 | NH$_2$ | H | Br | 2HCl Acetone Solvate | 170-210° (dec.) | — |
| 167 | NHAc | H | Br | l- | 195-197° | −15.3° (c=2.6, MeOH) |
| 168 | NH$_2$ | H | Br | l- | 175-177° | [α]$^{25}$ = 43.6- 44.5° (c=2.6, MeOH) |
| 169 | NH$_2$ | H | NO$_2$ | l- HCl Acetone Solvate | 140-210° | — |

| | % Calculated | | | | | % Found | | | | |
|---|---|---|---|---|---|---|---|---|---|---|
| Example | C | H | N | S | Other | C | H | N | S | Br | Cl |
| 164 | 36.23 | 3.04 | 11.53 | 8.79 | Br 21.92 Cl 9.72 | 35.97 | 2.96 | 11.40 | 8.52 | 22.09 | 9.50 |
| 165 | 44.30 | 4.06 | 14.09 | 10.75 | 26.80 | 44.19 | 4.03 | 14.06 | 10.93 | 26.65 | |
| 166 | 35.60 | 3.80 | 11.32 | 8.64 | | 35.52 | 3.95 | 10.75 | 8.17 | | |
| 167 | 45.89 | 4.15 | 12.35 | 9.43 | Br 23.49 | 46.15 | 3.85 | 12.50 | 9.45 | 23.82 | — |
| 168 | 44.30 | 4.06 | 14.04 | 10.75 | Br 26.80 | 44.10 | 4.02 | 13.96 | 10.75 | 26.58 | |
| 169 | 46.74 | 5.21 | 15.58 | 8.92 | Cl 9.86 | 45.20 | 4.99 | 15.68 | 9.08 | — | 11.79 |

[a]Racemic compounds unless noted in X' column.

TABLE VI 6,7,Dihydro-6-phenyl-5H-imidazo[2,b]thiazole Derivatives[a]

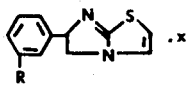

| Example | R | X | Melting Point | Empirical Formula | % Calculated | | | | % Found | | | |
|---|---|---|---|---|---|---|---|---|---|---|---|---|
| | | | | | C | H | N | S | C | H | N | S |
| 170 | HN—CO—CH(CH$_3$)$_2$ | — | 175-178 | N$_3$SOC$_{15}$H$_{17}$ | 62.69 | 5.96 | 14.62 | 11.16 | 63.49 | 6.04 | 14.39 | 10.52 |
| 171 | HN—CO—C(CH$_3$)$_3$ | — | 163-165 | N$_3$SOC$_{16}$H$_{19}$ | 63.76 | 6.35 | 13.94 | 10.64 | 63.62 | 6.25 | 14.01 | 10.54 |
| 172 | HN—CO—H | — | 162-164 | N$_3$SOC$_{12}$H$_{11}$ | 58.8 | 4.53 | 17.15 | — | 58.59 | 4.62 | 17.04 | — |
| 173 | HN-CO-⟨phenyl⟩ | HCl | 207-209 | N$_3$SOC$_{18}$H$_{15}$·HCl | 59.49 | 4.31 | 11.21 | — | 59.73 | 4.51 | 10.96 | — |

[a]Racemic compounds unless noted otherwise.

EXAMPLE 174

Albino female mice are each inoculated with about 20 infectious larvae of Nematospiroides dubius. This nematode is a representative of the economical important trichostrongylis worms of ruminants and other hosts, and of nematodes in general. Twenty-two days after inoculation, groups of four randomly selected mice containing adult N. dubius are given single oral doses of test compounds dissolved or suspended in 0.4 ml. of water per 20 gram mouse. At 26 or 27 days after inoculation, treated mice and in each test four randomly selected groups of untreated mice are necropsied. The number of worms in the small intestine of each mouse are determined by microscopic examination. Average worm numbers for each treated group and for the untreated controls are computed and the percent efficacy determined by the customary formula:

(Average Worms in Control - Average Worms in Treated)/(Average Worms in Control) X 100.

Using the above procedure, (Table II) hereinafter gives results from representative tests with dl-m-aminotetramisole, 6-(m-aminophenyl)-2,3,5,6-tetrahydroimidazo[2,1-b]thiazole dihydrochloride. Each result in (Table II) represents one group of treated mice. The total results show that the approximate dose which removes 50% of the worms, the $ED_{50}$, is 1.0 mg./kg. This indicates unusually high activity for the tetramisole type compound.

TABLE VII

% Efficacy of dl-m-amino Tetramisole Versus N. dubius by Single Oral Dose

| Dose Mg./Kg. | % Efficacy per Group | Average % Efficacy |
|---|---|---|
| 10 | 100; 100; 100 | 100 |
| 5 | 100; 100 | 100 |
| 4 | 100; 100; 100; 100; 100 (100; 100) | 100 |
| 2.0 | 77; 78; 82; 82; 83; 88; 92; 98 | 85 |
| 1.25 | 80; 82 | 81 |
| 1.00 | 29; 29; 49; 57; 59; 77 | 50 |
| 0.5 | 2; 6; 8 | 5 |

EXAMPLE 175

Data obtained by the above procedures (Example 174) for the unsubstituted dl-tetramisole in mice against *N. dubius* show an $ED_{50}$ of about 9 mg./kg. (Table VIII hereinafter). Accordingly, m-aminotetramisole is approximately nine times as active as tetramisole. The dose required to attain 85 – 88% efficacy also indicates approximately eightfold superiority of the m-amino compound.

Table VIII

% Efficacy of dl-Tetramisole Versus N. Dubius by Single Oral Dose

| Dose Mg./Kg. | % Efficacy per Group | Average % Efficacy |
|---|---|---|
| 20 | 96; 96; 98; 99; 99; 100 | 98 |
| 16 | 74; 91; 92; 94 | 88 |
| 12 | 60; 62; 68; 73 | 66 |
| 10 | 49; 58; 63; 67; 70; 74; 77; 77; 79; 83 | 70 |
| 8 | 28; 33; 33; 39 | 33 |
| 6 | 0; 0; 0; 0; 19; 24 | 7 |

EXAMPLE 176

Data on the acute oral toxicity to mice of various single oral doses of the above compounds and several analogs were obtained by conventional procedures, (Table IX hereinafter). These m-amino and substituted m-amino analogs of tetramisole are considerably more toxic than tetramisole in agreement with their higher anthelmintic activity against *N. dubius*. However, all compounds including tetramisole have a similar chemotherapeutic index, i.e., $LD_{50}/ED_{50}$, of ten- to twentyfold. All compounds were well tolerated at dosages required for complete worm removal.

Table IX

Mouse Oral Toxicity and $ED_{50}$ vs. N. dubius of Various Tetramisoles Mg./Kg.

| Phenyl Substituent | None | m-NH$_2$ | m-NH$_2$ | m-NH—HCO | m-NH—CH$_3$ | m-NH—CO—CH$_3$ | 5,6-dihydro m-NH$_2$[a] |
|---|---|---|---|---|---|---|---|
| Stereo Isomer | dl | dl | l | dl | dl | dl | dl |
| Dose Mg./Kg. | | | | | Dead/Total | | |
| 300 | 10/10 | | | | | | |
| 200 | 15/20 | | | | | | |
| 150 | 8/30 | | | | | | |
| 100 | 1/10 | | | | 2/5 | | |
| 50 | | | | | 0/4 | | |
| 40 | | 4/4 | | 12/13 | | | |
| 20 | | 10/12 | 4/5 | 1/10 | 0/4 | | |
| 15 | | 7/14 | 3/9 | | | | |
| 10 | | 2/29 | 2/10 | 0/4 | | | |
| 4–5 | | 0/8 | 0/12 | 0/8 | | | |
| Approx. $LD_{50}$ | 175 | 15 | 15 | 30 | 100 | >10 | 10 |
| Approx. $ED_{50}$ | 9 | 1 | .75 | 3 | 7 | 3–4 | 1.5 |
| Approx. $LD_{50}/ED_{50}$ | 19 | 15 | 20 | 10 | 14 | | |

[a]All other compounds 2,3,5,6-tetrahydroimidazothiazoles; this compound is a 5,6-dihydro-imidazo[2,1-b]thiazole.

| Phenyl Substituent | m-NH—CO—C$_2$H$_5$ | m-NH—CO—C$_3$H$_{7n}$ | m-NH—CO—CH(CH$_3$)$_2$ | m-NH—CO—CH(CH$_3$)$_2$ | m-NH—CO—C(CH$_3$)$_3$ |
|---|---|---|---|---|---|
| Stereo Isomer | dl | dl | dl | l | dl |
| Dose Mg./Kg. | | | Dead/Total | | |
| 200 | | | | | 5/6 |
| 160 | | | | | |
| 150 | | | | | |
| 120 | | | 6/6 | | |
| 100 | 6/6 | 5/5 | | 8/8 | 2/6 |
| 80 | 5/5 | 4/5 | 5/6 | | |
| 60 | 4/6 | 4/5 | | | |
| 50 | | | | 2/8 | 0/6 |
| 40 | 4/5 | 3/5 | 1/6 | | |
| Approx. $LD_{50}$ | <40 | 40 | ~60 | 50 | 100 |
| Approx. $ED_{50}$ | 2 | 2 | 3 | 1 | 3 |
| Approx. $LD_{50}/ED_{50}$ | 20 | 20 | 20 | 50 | 33 |

| Phenyl Substituent | m-NH—CO—C(CH$_3$)$_2$ | H | m-NH—CO—CH(C$_2$H$_5$)$_2$ | m-NH—CO—⟨phenyl⟩ | m-NH—CO—OCH$_3$ | m-NH—CO—OCH$_3$ | m-NH—CH(CH$_3$)$_2$ |
|---|---|---|---|---|---|---|---|
| Stereo Isomer | l | | dl | dl | dl | l | dl |
| Dose Mg./Kg. | | | | Dead/Total | | | |
| 200 | 6/6 | | | | 5/5 | 5/5 | |
| 180 | | | 3/6 | | | | |
| 150 | | | | | 3/5 | 1/5 | |
| 120 | | | 0/6 | 5/6 | | | |
| 100 | 2/6 | | | | 0/5 | 0/5 | 5/6 |
| 80 | | | 0/6 | 4/6 | | | 4/6 |
| 60 | | | | 3/6 | | | 3/6 |
| 50 | 0/6 | | | | 0/5 | 0/5 | |
| 40 | | | | 0/6 | | | 2/6 |

Table IX-continued

Mouse Oral Toxicity andd $ED_{50}$ vs. N. dubius of Various Tetramisoles Mg./Kg.

| Phenyl Substituent<br>Stereo Isomer<br>Dose Mg./Kg. | None<br>dl | m-$NH_2$<br>dl | m-$NH_2$<br>l | m-NH—HCO<br>dl | m-NH—$CH_3$<br>dl<br>Dead/Total | m-NH—CO—$CH_3$<br>dl | 5,6-dihydro m-$NH_2$<sup>a</sup><br>dl |
|---|---|---|---|---|---|---|---|
| Approx. $LD_{50}$ | 100 | 160 | | 60 | 150 | ~150 | ~40 |
| Approx. $ED_{50}$ | 1 | 75 | | 1 | 15 | 75 | 5 |
| Approx. $LD_{50}/ED_{50}$ | 100 | 21 | | 60 | 10 | 20 | 8 |

[Structure: phenyl ring with $R_4$ substituent and N-$R_1$/H substituent, attached to tetrahydroimidazothiazole ring system]

| Dose Mg./Kg. | Dead/Total | | |
|---|---|---|---|
| | $R_1$=H $R_4$=$NO_2$ | $R_1$=H $R_4$=Br | $R_1$=COCH$_3$ $R_4$=Br |
| 240 | 6/6 | | |
| 120 | 2/6 | | |
| 80 | | 6/6 | |
| 60 | 0/6 | | |
| 40 | | 2/6 | |
| 20 | | 0/6 | |
| Approx. $LD_{50}$ | 120 | 40 | >100 |
| Approx. $ED_{50}$ | 2 | 5 | 30 |
| Approx. $LD_{50}/ED_{50}$ | 60 | 8 | |

EXAMPLE 177

Using the procedures of Example 174, the approximate single dose oral $ED_{50}$ values against N. dubius in mice were determined for tetramisole and analogs with various substituents on its phenyl ring (Table X hereinafter). The unexpected high activity of dl-m-amino tetramisole is attributable to its laevo component; and not only amino, but also various substituted amino groups in the meta position increased activity over tetramisole. Identical substituents in the para or ortho positions were less active than tetramisole; as were other types of substituents in the meta position. Particularly noteworthy was higher quantitative activity than for the meta-nitro analogs.

Table X

Comparative Oral Efficacy of Various Tetramisoles Against N. dubius

| Stereo Isomer | Salt | Substituent on Phenyl | $ED_{50}$ meta | Approx. Mg./Kg/ as Base para | ortho |
|---|---|---|---|---|---|
| dl | HCl | (H) | 9 | 9 | 9 |
| dl | 2HCl | $NH_2$ | 1 | — | >100 |
| l | 2HCl | $NH_2$ | 0.75 | >10 | — |
| d | 2HCl | $NH_2$ | 10 | >20 | — |
| dl | Base | NH—HCO | 3 | — | — |
| l | Base | NH—HCO | — | >10 | — |
| d | Base | NH—HCO | — | >40 | — |
| dl | Base | NH—CO—$CH_3$ | 4 | — | — |
| dl | 2HCl | NH—$CH_3$ | 7 | — | — |
| l | 2HCl | NH—$CH_3$ | — | >50 | — |
| dl | Base | N=C=S | 20 | — | — |
| dl | HCl | $NO_2$ | 15 | — | >100 |
| l | HCl | $NO_2$ | 12 | 40 | — |
| d | HCl | $NO_2$ | >30 | >200 | — |
| dl | $HClO_4$ | $NO_2$* | 25 | — | — |
| dl | 2HCl | $NH_2$ | 1.5 | — | — |
| dl | | OH | >10 | — | — |
| dl | HBr | $OCH_3$ | >10 | — | — |

Table X-continued

Comparative Oral Efficacy of Various Tetramisoles Against N. dubius

| Stereo Isomer | Salt | Substituent on Phenyl | $ED_{50}$ meta | Approx. Mg./Kg/ as Base para | ortho |
|---|---|---|---|---|---|
| dl | HCl | $CH_3$ | >10 | — | — |
| dl | HCl | NH—CO—$C_2H_5$ | 2 | — | — |
| dl | HCl | NH—CO—$C_3H_7$n | 2 | — | — |
| dl | HCl | NH—CO—CH($CH_3$)$_2$ | 3 | — | — |
| l | HCl | NH—CO—CH($CH_3$)$_2$ | 1 | — | — |
| dl | Base | NH—CO—CH($CH_3$)$_2$ | 7.5 | — | — |
| dl | HCl | NH—CO—C($CH_3$)$_3$ | 3 | — | — |
| l | HCl | NH—CO—C($CH_3$)$_3$ | 1 | — | — |
| dl | Base | NH—CO—* C($CH_3$)$_3$ | 7.5 | — | — |
| dl | HCl | NH—CO—CH—($C_2H_5$)$_2$ | 7.5 | — | — |
| dl | HCl | NH-CO-(phenyl) | 1 | — | — |
| dl | HCl | NH—CO—$OCH_3$ | 15 | — | — |
| l | HCl | NH—CO—$OCH_3$ | 7.5 | — | — |
| dl | HCl | NH—CH($CH_3$)$_2$ | 5 | — | — |

>Indicates inactive at dose shown.
*This compound, 5,6-dihydro imidazothiazole - all others 2,3,5,6-tetrahydro.

Table X-continued
Comparative Oral Efficacy of Various Tetramisoles Against N. dubius

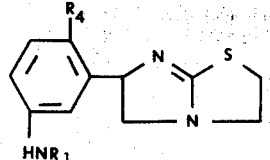

| Stereo Isomer | Salt | Substituent on Phenyl | ED$_{50}$ meta | para | ortho |
|---|---|---|---|---|---|
| | | | Approx. Mg./Kg. as Base | | |

| Stereo Isomer | Salt | R$_1$ | R$_4$ | ED$_{50}$ |
|---|---|---|---|---|
| dl | HCl | H | NO$_2$ | 2 |
| dl | HCl | H | Br | 5 |
| dl | HCl | —COCH$_3$ | Br | 30 |

EXAMPLE 178

Dogs infected with mature adult whipworms *Trichuris vulpis* were treated with various single or double doses of unsubstituted or substituted tetramisole analogs by the oral or subcutaneous route (Table XI hereinafter). Whipworms passed in the feces were collected for several days, and the whipworms still present determined at necropsy. Percent efficacy was determined in these "critical" tests. The meta-amino analogs had surprisingly higher activity than unsubstituted tetramisole with oral or subcutaneous doses which were non-toxic for the dogs. Trichuris is a type of nematode refactory to treatment with most prior anthelmintics at well tolerated doses. Taxonomically allied nematodes, e.g., Trichinella and Capillaria are also refractory to most anthelmintics.

Table XI
Comparative Oral or Subcutaneous (SC) Activity vs. Mature Trichuris vulpis in Dogs

| Stereo Isomer | Meta Substituent on Phenyl | Maximum Non-Lethal Dose for Dog Mg./Kg. Oral | SC | % Efficacy Orally at Mg./Kg. of 5 | 2.5 | 1.25 | % Efficacy SC at Mg./Kg. 20 | 15 | 10 | 5 | 2.5 | 1.25 |
|---|---|---|---|---|---|---|---|---|---|---|---|---|
| dl | H | >20 | 25 | (>10 mg./kg.)$^2$ | — | — | — | — | 2 (3) | — | | |
| l | H | | 30 | — | | | 100 (2)$^r$ | 43 (2)$^r$ | 50 (7) | 8 (2) | — | |
| dl | NH$_2$ | 7.5 | 5 | 98 | 99 (2) | | — | — | — | 100 (3)$^u$ | 92 (2) | — |
| l | NH$_2$ | 10 | 4 | 100 | 100 (2) | 94 (3) | | | | — | 100 (2) | 72 (4) |
| dl | NH—HCO | 7.5 | >5 | 100 | 83 (2) | 21 | | | | | | |
| l | NH—HCO | 2.5 | | | 100 (2) | 46 (4)$^b$ | | | | | | |
| dl | NH—CH$_3$ | >10 | 30 | 100 | | | | | | | 94 | 29 |

$^a$ Other values in ( ) equal number od dogs when more than one. % Efficacy based on total worms removed and present in all dogs at each dose shown.
> Means inactive at dose shown.
$^b$ Average dose 1.5 (1.25-1.75)
$^r$ Total dose given twice a day.
$^u$ Two dogs single dose, other total twice a day dose.

TABLE XII
Activity and Toxicity of Meta-Amino Analogs of Tetramisole in Mice

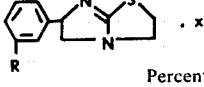

| R$^{(=)}$ | X | LD$_{50}$ (mg./Kg.) | 0.625 | 1.25 | 2.0 | 4.0 | 5.0 | 7.5 | 10.0 | 20 | 30 | 40 | 50 | 60 | 100 |
|---|---|---|---|---|---|---|---|---|---|---|---|---|---|---|---|
| NH$_2$ | 2HCl | ~20 | — | 57 | 92 | 100 | 100 | — | 100 | — | — | — | — | — | — |
| NH$_2$ l- | 2HCl | ~15 | — | 59 | 88 | 98 | — | — | — | — | — | — | — | — | — |
| HNCH$_3$ | 2HCl | — | — | — | 28 | — | — | — | 66 | 100 | 100 | — | — | — | — |
| HN—CH(CH$_3$)$_2$ | 2HCl acetone solvate | ~50 | — | — | — | — | 55 | 89 | 100 | 100 | — | 100 | — | — | — |
| HN—CH(CH$_3$)CH$_2$OH | — | — | — | — | — | — | 1 | — | 1 | — | — | — | 67 | — | — |
| HN-CH$_2$-C$_6$H$_5$ | — | — | — | — | — | — | 56 | — | 91 | 95 | — | — | — | — | — |
| HN-CH$_2$-C$_6$H$_4$-OCH$_3$ | — | — | — | — | — | — | i | — | 40 | 100 | — | — | 100 | — | 100 |
| HN-CH$_2$-pyridyl | — | — | — | — | — | — | 44 | — | 96 | — | — | — | — | — | — |
| CH$_3$N—CH(CH$_3$)$_2$ | — | ~40-60 | — | — | — | — | — | — | i | — | 78 | — | 88 | — | |
| HN—CO$_2$CH$_3$ | HCl | ~125 | — | — | — | — | — | — | 25 | 96 | 100 | — | — | — | |
| HN—CO$_2$CH$_3$ l- | HCl | ~125 | — | — | — | — | 28 | — | 61 | 100 | — | 100 | — | — | — |
| HNCHO | — | ~30 | — | — | — | 79 | — | — | 97 | — | — | — | — | — | — |
| HNCHO l- | — | ~30 | — | 61 | 72 | — | 95 | — | 100 | — | — | — | — | — | — |
| (CH$_3$)$_2$CH—N—CHO | — | — | — | — | — | — | — | — | i | — | 99 | — | 100 | — | |
| HN—CO—CH$_3$ | HCl | ~40-60 | — | — | — | 66 | — | — | 100 | — | — | — | — | — | |
| H—N—CO—CH$_3$ l- | HCl | — | — | — | — | 51 | — | — | 100 | — | — | — | — | — | |
| H—N—CO—CH$_2$Cl | — | ~50-60 | — | 84 | — | — | 100 | — | — | — | — | 100 | 100 | — | |

TABLE XII-continued

Activity and Toxicity of Meta-Amino Analogs of Tetramisole in Mice

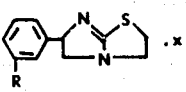

| R(=) | X | LD$_{50}$ (mg./Kg.) | \multicolumn{12}{c}{Percent Nematospiroides (Activity (**)) Single Oral Dose (mg./Kg.)} | | | | | | | | | | | |
|---|---|---|---|---|---|---|---|---|---|---|---|---|---|---|
| | | | 0.625 | 1.25 | 2.0 | 4.0 | 5.0 | 7.5 | 10.0 | 20 | 30 | 40 | 50 | 60 | 100 |
| H—N—CO—CH$_2$CH$_3$ | HCl .H$_2$O | ~30–40 | — | — | 76 | — | 100 | — | 100 | — | — | — | — | — | — |
| H—N—CO—(CH$_2$)$_2$CH$_3$ | HCl .H$_2$O | ~30–40 | — | 43 | 58 | — | 99 | — | 100 | — | — | — | — | — | — |
| H—N—CO—CH(CH$_3$)$_2$ | HCl .H$_2$O | ~75 | — | — | — | — | 99 | — | 100 | 100 | — | — | — | — | — |
| H—N—CO—CH(CH$_3$)$_2$ l- | HCl | ~60–75 | 30 | 77 | 96 | — | 100 | 97 | 100 | — | — | — | — | — | — |
| H—N—COC(CH$_3$)$_3$ | HCl .H$_2$O | ~100 | — | — | i | — | 75 | — | 88 | 100 | — | — | — | — | — |
| HN—CO—C(CH$_3$)$_3$ l- | HCl | ~100 | — | 60 | 69 | — | 90 | — | 100 | — | — | — | — | — | — |
| HNCOCH$_2$C(CH$_3$)$_2$ | HCl | ~80–100 | — | — | i | — | 59 | — | 98 | — | — | — | — | — | — |
| HN—COCH(CH$_2$CH$_3$)$_2$ | HCl .H$_2$O | ~160 | — | — | — | — | — | — | 85 | 99 | — | 100 | — | — | — |
| HNCO(CH$_2$)$_5$CH$_3$ | HCl .H$_2$O | ~20–25 | i | 53 | 99 | — | 100 | — | 100 | — | — | — | — | — | — |
| H-N-CO-C$_6$H$_5$ | HCl | ~30 | — | 46 | 88 | — | 100 | — | 100 | — | — | — | — | — | — |
| H-N-CO-CH$_2$-C$_6$H$_5$ | — | — | — | — | — | 44 | — | 76 | — | 95 | — | — | — | — | — |
| H-N-CO-CH=CH-C$_6$H$_5$ | — | ~90 | — | 60 | 67 | — | 100 | — | 100 | — | — | — | — | — | — |
| HN-CO-C$_6$H$_5$ | HCl .H$_2$O | ~60 | — | 67 | 94 | — | 100 | — | 100 | 100 | — | — | — | — | — |
| H-N-CO-C$_6$H$_5$ l- | HCl | ~50–60 | 63 | 94 | 100 | — | — | — | — | — | — | — | — | — | — |
| HN-CO-C$_6$H$_4$-OCH$_3$ | HCl | ~60–80 | 56 | 58 | 95 | — | 100 | — | — | — | — | — | — | — | — |
| HN-CO-C$_6$H$_4$-Cl | — | ~80 | 40 | 63 | 90 | — | 100 | — | — | — | — | — | — | — | — |
| HN-CO-C$_6$H$_4$-Cl (meta) | — | ~80–100 | 40 | 52 | 95 | — | 97 | — | — | — | — | — | — | — | — |
| HN-CO-C$_6$H$_3$-Cl$_2$ | — | ~80–100 | 58 | 52 | 92 | — | 95 | — | — | — | — | — | — | — | — |
| HN-CO-C$_6$H$_4$-NO$_2$ | — | ~60–90 | — | 65 | 78 | — | 100 | — | 100 | — | — | — | — | — | — |
| HN-CO-naphthyl | — | — | — | — | — | — | — | i | — | — | — | — | — | — | 100 |
| HN-CO-furyl | HCl | ~80–100 | — | — | 37 | — | 85 | — | 99 | 100 | — | — | — | — | — |

TABLE XII-continued

Activity and Toxicity of Meta-Amino Analogs of Tetramisole in Mice

| R(*) | X | LD$_{50}$ (mg./Kg.) | Percent Nematospiroides (Activity (**)) Single Oral Dose (mg./Kg.) | | | | | | | | | | | | |
|---|---|---|---|---|---|---|---|---|---|---|---|---|---|---|---|
| | | | 0.625 | 1.25 | 2.0 | 4.0 | 5.0 | 7.5 | 10.0 | 20 | 30 | 40 | 50 | 60 | 100 |
| HN-CO-(adamantyl) | — | — | — | — | — | 68 | — | 65 | — | 85 | 100 | — | — | — | — |
| H—N—SO$_2$CH$_3$ | — | — | — | — | — | — | — | i | — | — | — | — | — | — | 100 |

(*)Racemic mixtures unless noted otherwise.
(**)Dose rates and LD$_{50}$ adjusted to give molar equivalents of tetramisole free base.
~ = about

TABLE XIII

Activity and Toxicity of Disubstituted Meta Amino Analogs of Tetramisole in Mice

| R* | X | LD$_{50(mg./Kg.)}$ | Percent Nematospirides Activity** Single Oral Dose (mg./Kg.) | | | | | | | | | | |
|---|---|---|---|---|---|---|---|---|---|---|---|---|---|
| | | | 0.625 | 1.25 | 2.0 | 4.0 | 5.0 | 10 | 20 | 30 | 40 | 50 | 60 | 100 |
| 2-Br, 5-NH$_2$-phenyl | 2HCl .acetone | ~50 | — | — | i | 43 | — | 100 | — | — | — | — | — | — |
| 2-Br, 5-NH$_2$-phenyl | 1- | — | — | — | — | — | — | — | i | — | 37 | — | — | 97 | — |
| 2-Br, 5-NHCOCH-phenyl | 1- | — | — | — | — | — | — | — | i | — | — | — | 100 | — | 100 |
| 2-NO$_2$, 5-NH$_2$-phenyl | HCl | ~120–140 | — | — | 43 | 89 | — | 100 | — | — | — | — | — | — |

*Racemic mixtures unless noted otherwise.
** Dose rates and LD$_{50}$ adjusted to give molar equivalents of tetramisole free base.

TABLE XIV

Activity and Toxicity of Meta Substituted 5,6-Dihydro-6-Phenyl Imidazo (2,1-b) thiazoles

| R* | X | LD$_{50}$(mg./Kg.) | Percent Nematospirides Activity** Single Oral Dose (mg./Kg.) | | | | | | | | | | |
|---|---|---|---|---|---|---|---|---|---|---|---|---|---|
| | | | 1.0 | 2.0 | 2.5 | 4.0 | 5.0 | 10 | 20 | 30 | 40 | 50 | 60 | 100 |
| NH$_2$ | — | ~80 | i | 53 | — | — | 96 | 100 | — | — | — | — | — | — |
| HNCHO | — | ~150 | — | — | i | 64 | — | 100 | — | — | — | — | — | — |
| HN-CO-CH(CH$_3$)$_2$ | — | — | — | — | i | — | 32 | 68 | — | — | — | — | — | — |
| HN-CO-C(CH$_3$)$_3$ | — | — | — | — | i | — | 35 | 80 | — | — | — | — | — | — |
| HN-CO-phenyl | — | ~120 | — | — | 73 | — | 94 | 100 | — | — | — | — | — | — |

*Racemic mixtures unless noted otherwise.
**Dose rates and LD$_{50}$ adjusted to give molar equivalents of tetramisole free base.

We claim:

1. A method for controlling gastrointestinal nematodes in warm-blooded animals comprising administering to said animals, a nematocidally effective amount of a compound of the formula:

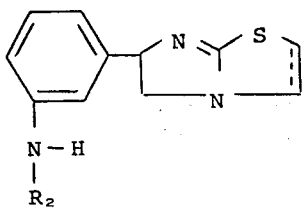

wherein $R_2$ is selected from the group consisting of naphthoyl, furoyl and adamantyl carbonyl, and    is a single or double bond and the pharmaceutically acceptable salts thereof.

2. A method according to claim 1, wherein the said compound is 3'-(2,3,5,6-tetrahydroimidazo[2,1-b]thiazol-6-yl)-2-furanilide hydrochloride.

3. A method according to claim 1, wherein the said compound is 3'-(2,3,5,6-tetrahydroimidazo[2,1-b]thiazol-6-yl-1-naphthanilide.

4. A method according to claim 1, wherein the said compound is 3'-(2,3,5,6-tetrahydroimidazo[2,1-b]thiazol-6-yl)-1-adamantanecarboxanilide.

* * * * *